United States Patent
Salamone et al.

(10) Patent No.: US 8,877,882 B1
(45) Date of Patent: Nov. 4, 2014

(54) NON-SELF-ADHERENT COATING MATERIALS

(71) Applicant: Rochal Industries, LLP, San Antonio, TX (US)

(72) Inventors: Joseph Charles Salamone, San Antonio, TX (US); Katelyn Elizabeth Reilly, San Antonio, TX (US); Ann Beal Salamone, San Antonio, TX (US); Xiaoyu Chen, San Antonio, TX (US)

(73) Assignee: Rochal Industries LLP, San Antonio, TX (US)

( * ) Notice: Subject to any disclaimer, the term of this patent is extended or adjusted under 35 U.S.C. 154(b) by 0 days.

(21) Appl. No.: 14/046,591

(22) Filed: Oct. 4, 2013

(51) Int. Cl.
*C08F 30/08* (2006.01)
*A61F 13/00* (2006.01)
*C08L 15/00* (2006.01)
*A61L 26/00* (2006.01)

(52) U.S. Cl.
CPC .......... *A61L 26/0014* (2013.01); *A61L 26/0066* (2013.01)
USPC ............. 526/279; 524/356; 602/52; 523/111; 523/118

(58) Field of Classification Search
CPC ......... C08F 30/08; A61F 13/00; A61F 26/14; A61F 26/26; A61F 26/66; C08L 15/00
USPC ............. 526/279; 602/52; 524/356; 523/111; 523/118
See application file for complete search history.

(56) References Cited

U.S. PATENT DOCUMENTS

| | | | |
|---|---|---|---|
| 4,152,508 A | 5/1979 | Ellis et al. | |
| 4,987,893 A | 1/1991 | Salamone et al. | |
| 5,103,812 A | 4/1992 | Salamone et al. | |
| 5,288,827 A * | 2/1994 | Li et al. ............ | 526/279 |
| 5,591,442 A | 1/1997 | Diehl et al. | |
| 5,858,937 A | 1/1999 | Richard et al. | |
| 6,143,805 A | 11/2000 | Hickey et al. | |
| 6,183,593 B1 | 2/2001 | Narang et al. | |
| 6,358,503 B1 | 3/2002 | Gerrish | |
| 6,383,502 B1 | 5/2002 | Dunshee et al. | |
| 7,641,893 B2 | 1/2010 | Salamone et al. | |
| 7,795,326 B2 | 9/2010 | Salamone et al. | |
| 8,197,803 B2 | 6/2012 | Salamone et al. | |
| 8,263,720 B1 | 9/2012 | Salamone et al. | |
| 8,415,404 B2 | 4/2013 | Nicolson et al. | |
| 8,491,881 B2 | 7/2013 | Salamone et al. | |
| 2007/0087113 A1 * | 4/2007 | Uilk et al. ............ | 427/2.1 |
| 2008/0114096 A1 | 5/2008 | Qu et al. | |
| 2010/0137472 A1 | 6/2010 | Ou-Yang | |

* cited by examiner

*Primary Examiner* — Michael M Bernshteyn
(74) *Attorney, Agent, or Firm* — Duane Morris LLP; J. Rodman Steele, Jr.; Gregory M. Lefkowitz

(57) ABSTRACT

Liquid adhesive coating materials are prepared that protect surfaces, such as medical devices and biological surfaces, including skin and mucous membranes, from pressure, shear, and friction. The liquid coating materials utilize an amphiphilic siloxysilane/hydroxyalkyl ester polymer-containing coating material dissolved in a volatile solvent, with or without an antimicrobial agent, where when the polymer coating is formed after solvent evaporation and is folded against itself or placed against another material, the surface of said coating does not adhere, while the bottom of the coating remains attached to the original surface.

29 Claims, No Drawings

NON-SELF-ADHERENT COATING MATERIALS

FIELD OF THE INVENTION

This invention relates generally to liquid adhesive materials that are useful for protecting surfaces, such as medical devices and biological surfaces, including skin and mucous membranes, from pressure, shear, and friction, and where antimicrobial compositions also protect against microorganisms.

BACKGROUND

Liquid bandages have become popular in recent years because of their ease of use in topical applications of protecting skin and/or of preventing damage to skin by forming conformal, topical coatings. Such applications have been from polymer coatings that are delivered from soluble solutions in volatile solvents including non-stinging solvents to skin and open wounds, such as hexamethyldisiloxane (HMDS), and isooctane (2,2,4-trimethylpentane), as well as stinging alcohol-based solvents, such as isopropanol and ethanol, for inherent antimicrobial character and the potential to solubilize many antimicrobial agents. While such polymer coatings are typically water insoluble, other coatings can be delivered from water utilizing water-soluble polymers and which, consequently, will redissolve in water.

Alkylsiloxysiloxane-containing hydrophobic polymers have been admixed with liquid polydimethylsiloxanes (U.S. Pat. No. 5,103,812 and U.S. Pat. No. 4,987,893) to provide non-stinging, non-irritating coating materials that allow body fluid evaporation and oxygen permeability while protecting the body surface from further contamination and desiccation. In another variation, alkylsiloxysiloxane-containing polymers were admixed with 2,2,4-trimethylpentane to provide similar non-stinging coating properties (U.S. Pat. No. 6,383,502). These coatings have the common disadvantages of loss of adhesion toward hydrated surfaces, loss of adhesion in higher flexibility areas such as knuckles or knees, and being adherent surfaces to themselves or other objects at room temperature or body temperature. The primary alkylsiloxysilane monomer for these polymer coatings has been 3-methacryloyloxypropyltris(trimethylsiloxy)silane (TRIS, also known as 3-[tris(trimethylsiloxoy)silyl]propyl methacrylate).

A major difficulty with such coatings that has not been addressed has been their adhesion to undergarments, bed clothes, sheets, blankets, tubing, medical devices and dressings, as well as attachment to more than one portion of one's body, such as a folded arm, a folded leg, under a chin, or under a breast. When heated to body temperature, such coatings adhere to skin and to surfaces with which the polymer coated skin is in contact. In combination with external body temperature (33-37° C.) and pressure applied to different portions of the body, the air surface of the polymer coating can fold and adhere to itself, causing discomfort. In particular, if an individual is confined to bed and has limited mobility, the pressure of lying in one place for extended periods of time, combined with high shear forces when the person is raised or lowered on the bed, sliding against the bed sheets, the liquid bandage can adhere to the bed sheets and hence cause damage, particularly to fragile skin and wounds. This feature is a result of sustained pressure, friction, and shear. A similar problem can occur with medical devices where friction, pressure and shear forces can cause discomfort to a patient with movement.

As used herein, "medical device" has its plain meaning and includes objects whose surfaces contact skin, tissue, blood or other bodily fluids and components, as well as materials, such as sutures, needles, sheets, bed clothes, pillows, undergarments, blankets, cushions, towels, tubing, membranes, and the like, wherein such medical devices include, but are not limited to, catheters, such as dialysis catheters, central venous catheters, thoracic drain catheters, urinary catheters, and angioplasty balloon catheters; surgical implants, such as coronary stents; and prostheses, such as artificial limbs. Examples of suture materials include poly(glycolic acid), poly(lactic acid), poly(lactic-co-glycolic acid), polydioxanone, polycaprolactone, poly(3-hydroxybutyrate), silk, catgut, collagen, cotton, nylon, polyester, polypropylene, leather, and combinations thereof. Examples of tubing include tubing used with catheters and in intravenous or intra-arterial infusion and other surgical uses, as well as in whole blood oxygenators, and the like. Examples of membranes include hemodialysis membranes, blood oxygenation membranes, artificial pancreas membranes, and membranes used in diagnostic and biosensor devices. Examples of fabrics, such as clothes, sheets, blankets, towels, etc., are often composed of cotton, nylon, polyester, wool, nonwoven materials, polyethylene, polypropylene, combinations thereof, and biodegradable materials.

Additional medical devices include sponges, staples, tapes, clamps, leads, lead adapters, lead connectors, clips, covers, drapes, blood filters, temperature monitors, cannulae, implantable pumps, ostomy pouches, dialyzers, drainage products, electrodes, stethoscopes, fracture fixation devices, gloves, guide wires, pins, retention cuffs, screws, ceramics, biodegradable polymers, bioglass, poly(methyl methacrylate) materials, polyethylene materials, elastomers, surgical instruments, valves, balloons, batteries, orthopedic implants, pacemakers, plugs, plates, ports, prosthetic heart valves, shunts, and vascular access devices.

When a non-stinging application to a biological surface is not required, such as treating skin in areas prior to blister formation, such products can be alcohol based. A prominent example is New-Skin® Liquid Bandage from Prestige Bands, Inc., which contains an ester solvent (amyl acetate), an alcohol solvent (ethanol) that is also antimicrobial, a film forming polymer of nitrocellulose, a propellant of isooctane-propane, oils for lubricating and other health benefits, and added antimicrobial agents of benzethonium chloride and benzalkonium chloride.

A related liquid bandage product when a non-sting application is not preferred is Curad® Spray Bandage by Beiersdorf AG, composed of a film forming polymer of poly(methyl acrylate-isobutene-monoisopropyl maleate), in ethyl acetate, n-pentane, carbon dioxide, and menthol.

Another category of polymer useful as a liquid adhesive bandage, cycloalkyl methacrylate copolymers, has been found to be soluble in a mixture of liquid polydimethylsiloxanes, 2,2,4-trimethylpentane and isododecane (U.S. Pat. No. 6,358,503).

Cyanoacrylates have also found use as liquid adhesive bandages, particularly butyl and octyl cyanoacrylates (U.S. Pat. No. 6,183,593; U.S. Pat. No. 6,143,805). These materials provide quick film formation and are especially useful for closing thin wounds, such as those created by paper or razor cuts. Wounds that are in high flex areas are not suitable for treatment with cyanoacrylates as they tend to increase scarring, if well adhered, or to delaminate quickly, if not well adhered due to their intrinsic brittleness.

Water-soluble liquid bandages are also available for human, veterinary, and device use, such as JUC Liquid Bandage Spray from NMS Technologies that forms a positively charged antimicrobial coating. Another water-soluble liquid bandage, for veterinary use only, is Facilitator from IDEXX Pharmaceuticals, which is composed of water-soluble hydroxyethyl starch. A variety of poly(N-vinylpyrrolidone) water-based liquid bandages are also available for veterinary use. Whereas water-based liquid bandages are normally less traumatic when applied to an open wound than application of an organic solvent, the drying time of a polymer film deposited from water can be long, and it therefore may be difficult to form a polymer coating in a desired location because of water flow.

An antimicrobial coating composition for devices selected from the group of alkyl acrylates, alkyl methacrylates, alkyl hydroxyl(meth)acrylates, and alkyl methoxycinnamate acrylates has been reported in a mild solvent, including alcohols and hydrocarbons (U.S. Pat. Appl. 2010/0137472), wherein the coatings can be applied at 60° C. for 10 minutes or less.

Water- and alcohol-based liquid bandages also have the capability of solubilizing antimicrobial agents and active pharmaceutical agents, such that when a polymer coating is cast, the active agent is encapsulated within a polymer film, resulting in a sustained (controlled) release of the biologically active agent over time. Many such biological agents are often polar compounds and/or can be in salt form, facilitating solubility in polar solvents.

The use of alcohol-based solvents for liquid bandages containing an antimicrobial agent enhances the overall antimicrobial activity because of the innate biocidal behavior of alcohol solutions, primarily ethanol and isopropanol, particularly in the presence of water, wherein the water may emanate from added water to the liquid bandage solution, moisture in/on the skin or wound, moisture from the air, or from standing or moving water, such as from pools, rain, lakes, streams, rivers, tributaries, bays, oceans, and the like, wetting the skin, mucosal tissue, and, potentially, open wounds.

The addition of antimicrobial agents to coatings from liquid bandages has great importance in controlling infection and the deposition and growth of microorganisms in burns, in acute and chronic wounds, on surfaces of medical devices and dressings, in pre- and post-surgical coatings, and in all areas of the body where microorganisms can propagate.

SUMMARY

The present invention provides a liquid, amphiphilic siloxysilane/hydroxyalkyl ester polymer-containing coating material, with or without an antimicrobial agent, that can act as a bandage or coating on skin, on a device or on a dressing to prevent damage to wounds, skin or mucosal tissue resulting from applied pressure, friction, and shear forces.

It has unexpectedly been discovered that a unique combination of an amphiphilic polymer comprised of a siloxysilane monomer and a hydroxyalkyl ester monomer, with an overall low degree of covalent crosslinking of <0.4 weight % or less, is soluble in polar and non-polar solvents and when cast and dried yields an adherent polymer coating on a surface, particularly to a skin surface, wherein when the polymer coating is folded against itself or placed against another material, the surface of said coating does not adhere, while the bottom of the coating remains attached to the original surface. This phenomenon has not previously been observed in any hydrophobic (U.S. Pat. No. 5,103,812) or amphiphilic (U.S. Pat. No. 7,795,326) siloxysilane-based liquid bandage formulation of low covalent crosslinking, but has been observed in certain cyanoacrylate monomer formulations (U.S. Pat. No. 7,641,893).

Crosslinked polymer coatings containing a polysaccharide that display a hydrophilic, lubricious surface with low coefficients of friction are reported to not develop tack or have insignificant tack when applied to a medical device at temperatures between 100-120° C. (U.S. Pat. Appl. 2008/0114096).

The polymer coating of this invention is applied in liquid form and air dried at room or body temperature on a biological surface or medical device to form an adherent, water-insoluble, water-vapor permeable, oxygen permeable, conformal, non-biodegradable, solid, clear, protective film. Application of the coating solution can be by spraying, wiping, dipping, painting, casting, brushing, and by aerosol propellants, or by other conventional coating methods, to coat a surface or device. The liquid adhesive materials are useful for protecting surfaces, such as biological surfaces, including skin and mucous membranes, and medical devices. When an antimicrobial agent is added to the liquid bandage formulation, coating on a device or dressing additionally provides biocidal activity against microbial contamination and/or growth.

The polymer component of the liquid adhesive material comprises an amphiphilic polymer, said polymer comprises at least one polymerizable hydrophilic hydroxyalkyl ester-containing addition polymerizable monomer component whose homopolymer is swellable or soluble in water and at least one addition polymerizable siloxy-containing monomer component whose homopolymer is hydrophobic or amphiphilic and insoluble in water, and wherein said liquid coating material forms an adherent, conformable, non-biodegradable, water-vapor permeable, water-insoluble coating when applied to a surface, and wherein said volatile, liquid is selected from the group consisting of non-polar solvents comprising volatile linear and cyclic siloxanes, volatile alkanes, volatile cycloalkanes, volatile chlorocarbons and volatile fluorocarbons, and polar volatile solvents comprising volatile alcohols, volatile esters, volatile ketones, volatile ethers, and mixtures thereof, with and without water (when compatible and solubilized), and wherein said volatile liquid volatilizes at room or body temperature.

As used herein, a polymer is "soluble" or "solubilized" if the amount of polymer present in the solvent system is completely dissolved in the solvent system without the polymer forming a precipitate or visible, swollen gel particles in solution.

Because of the dual nature of the monomeric groups, i.e. hydrophilic for the hydroxyalkyl monomer component and hydrophobic or amphiphilic for the siloxysilane component, the overall polymer composition is amphiphilic. The polymer may also include other addition polymerizable monomers such that the resulting polymer film is non-adherent to itself or to another object. In some embodiments, the other addition polymerizable monomers can consist of either monomers that form hydrophilic homopolymers or monomers that form hydrophobic homopolymers. In other embodiments, the other additional polymerizable monomers can include both monomers that form hydrophilic homopolymers and monomers that form hydrophobic homopolymers. The cast and dried amphiphilic polymer coatings of this invention are insoluble in water, but the coatings allow for water vapor transmission and oxygen permeability, primarily by the siloxysilane monomer component. Siloxysilane-containing polymers are noted for their water vapor permeability and their gas permeability. Such polymers have been used in contact lens materials as crosslinked soft silicone hydrogels or as crosslinked rigid gas permeable materials because of their high oxygen permeability (U.S. Pat. No. 4,152,508; U.S. Pat. No. 7,795, 326; U.S. Pat. No. 8,415,404) and as liquid adhesive bandages because of their oxygen permeability and water-vapor transmission (U.S. Pat. No. 7,795,326).

Preferably the polymer is present and soluble from about 0.1% up to 50% by weight. In other embodiments, the polymer is present and soluble from about 1% to about 40% by weight, or by 2.5% to 30% by weight, and most preferably by 5% to 20% by weight. In some embodiments, the volatile liquid is present from about 50% up to 99.9% by weight, preferably, from about 60% to 99% by weight, or by 70% to 97.5% by weight, or from 80% to 95% by weight. The siloxysilane:hydroxyalkyl ester polymer forms a water-insoluble coating that can form a clear film when applied to a surface or the skin of a user, or to a device, or to a dressing, when cast from either a polar or non-polar volatile solvent.

If alcohol solvents are used for polymer solubility and for casting purposes, a small concentration of water can be added, particularly if polar biologically agents are used, to enhance solubility. In such circumstances, the water content can range from 0.1 to 20.5 weight %, with the requirement that both the solution and the cast film remain clear. After evaporation of the alcohol/water solvent, these cast polymer films are insoluble in water.

The amphiphilic character of the polymer coating facilitates its interaction with dry and moist surfaces. It is believed that the hydrophilic, hydroxyalkyl ester monomer component of the polymer is able to interact with moist surfaces by hydrogen bonding. It is believed that the coating is able to interact with a dry surface by its adhesive character from its siloxysilane component as well as by hydrogen-bonding of the hydroxyalkyl ester monomer component to any hydrophilic, hydrogen-bond accepting group.

The liquid composition and/or dried polymer film can have various antimicrobial agents, anti-infective agents, medicants or other biologically-active agents incorporated therein for maintaining sterility, or for agent release to the underlying surface, provided that the agent is soluble in the amphiphilic siloxysilane/hydroxyalkyl ester polymer coating formulation.

As used herein, "biologically-active agents" has its standard meaning and includes chemical substances or formulations that beneficially affect humans, animals, or plants or is intended for use in the cure, mitigation, treatment, prevention, or diagnosis of infection or disease, or is destructive to or inhibits the growth of microorganisms. The phrases "biologically-active agents" and "active agents" are used interchangeably herein. For example, such active agents comprise antibiotics, antibacterial agents, anti-infective agents, antifungal agents, antiprotozoal agents, anti-inflammatory agents, antiviral agents, antitumor agents, antibiotics, birth control agents, antipruritic agents, anti-smoking agents, motion-sickness agents, anesthetic agents, psoriasis agents, dermatitis agents, acne agents, astringent agents, chronic pain agents, non-steroidal anti-inflammatory (NSAIDs) agents, liposomes, lipid nanoparticles, blood pressure agents, heart regulating agents, steroids, saccharides, polysaccharides, nucleotides, peptides, growth factors, cytokines, and the like.

In some embodiments, the liquid polymer-containing coating material of this invention comprises a polymer from an addition polymerizable, hydrophilic hydroxyalkyl ester of a monomeric acid with an addition polymerizable hydrophobic or amphiphilic alkylsiloxysilane, arylsiloxysiloxane, or alkylarylsiloxysilane monomer(s). The hydroxyalkyl ester-containing monomer component increases the solubilization of a polar antimicrobial agent or biologically active agent, particularly in a polar volatile solvent, facilitating development of an antimicrobial liquid bandage or medicament-based liquid bandage. The material forms a coating or bandage in the form of a clear film when applied to a surface, device, dressing, or the skin of a user from a volatile liquid at room temperature or body temperature.

It is a further object of the invention to provide a non-adherent air surface to the polymer coating that does not adhere to skin, to itself, or to another material.

It is a further object of the invention to provide a polymer coating that reduces friction against another object.

It is a further object of the invention to provide a polymer coating that reduces shear applied by another object.

It is a further object of the invention to provide a liquid bandage polymer coating whose exposed surface remains non-adherent under body pressure.

In another aspect, the polymer, when solubilized in a volatile solvent, provides for a fast drying, adherent, flexible, breathable, water-insoluble, water vapor permeable, oxygen permeable, conformable coating or bandage.

It is an object of the invention to provide a liquid polymer-containing coating material that can act as a bandage to protect wounds and skin from being damaged, when applied in liquid form and air dried on the wound to form a conformal, adherent, solid protective film.

It is an object of this invention to provide a liquid bandage wherein the solvent is a volatile liquid that evaporates at room temperature or body temperature.

It is a further object of this invention that the volatile solvent is non-polar, polar, or a combination thereof.

It is a further object of the invention to provide a polymer film in which antimicrobial agents, active pharmaceutical agents, medicaments or other biologically-active agents, may be incorporated for gradual release onto targeted areas.

It is a further object of the invention to provide a polymer film in which antimicrobial agents are based upon chlorhexidine and its salts.

It is a further object of the invention to provide a polymer film in which antimicrobial agents are based upon alexidine and its salts.

It is a further object of the invention to provide a polymer film in which antimicrobial agents are based upon poly(hexamethylene biguanide) and its salts.

It is an object of this invention that the antimicrobial polymer coating compositions described herein can reduce or eliminate Gram positive and Gram negative bacteria in wounds, surfaces and devices.

It is an object of this invention that the antimicrobial polymer coating compositions described herein can reduce or eliminate yeast in wounds, surfaces and devices.

It is an object of this invention that the antimicrobial polymer coating compositions described herein can reduce or eliminate mold in wounds, surfaces and devices.

It is an object of this invention that the antimicrobial polymer coating compositions described herein can reduce or eliminate fungi in wounds, surfaces and devices.

It is an object of this invention that the antimicrobial polymer coating compositions described herein can reduce or eliminate protozoa in wounds, surfaces and devices.

It is an object of this invention that the antimicrobial polymer coating compositions described herein can reduce or eliminate viruses in wounds, surfaces and devices.

It is an object of this invention to provide a liquid bandage that includes a chelating agent.

It is an object of the invention to provide a liquid polymer-containing coating material that can be coated upon a device to reduce topical adherence of the device to skin or to a material when applied in liquid form and air dried to form a conformal, solid, protective film.

It is an object of the invention to provide an antimicrobial liquid polymer-containing coating material that can be coated upon a biological surface to reduce or eliminate Gram positive and Gram negative bacteria, fungi, protozoa, and viruses, when applied in liquid form and air dried to form a conformal, solid, protective film.

In another aspect of this invention, polymer coatings are provided that are useful for protecting biological surfaces against exogenous microbial contamination.

In another aspect, the polymer coating functions as the substrate for sustained (controlled) release of biologically-active agents.

It is a further object of the invention to provide a polymer coating that will prevent exogenous microorganism or particulate contamination to skin, mucous membranes, wounds, needles, catheters, surgical incision sites, surgical sutures, and internal and external medical devices.

It is a further object of the invention to provide a non-adherent surface to the polymer coating that does not attract debris and can remain clear for wound viewing as well as for cosmetic attractiveness.

It is a further object of the invention to provide a coating which, when applied, will control body fluid loss from an abraded area.

It is a further object of the invention to provide a low surface tension covering that can reduce drag against another object.

It is a further object of the invention to provide a coating on skin for adhesive trauma protection, including negative pressure wound therapy.

It is a further object of the invention to provide a coating which, when applied to skin, a device, or a dressing, is water-vapor permeable, but liquid water-insoluble.

It is a further object of the invention to treat acute and chronic wounds, as well as burn injuries.

It is a further object of the invention to provide a coating for protection at catheter insertion sites.

It is a further object of the invention to provide a coating for protection at screw, rod, pin, and brace skin penetration sites.

It is a further object of the invention to provide a coating for surgical incision sites.

It is an object of this invention that the antimicrobial polymer coating compositions provide a conformal, antimicrobial coating for pre- and post-surgical sites.

It is a further object of the invention to provide a coating for periwound skin protection.

It is a further object of the invention to provide a coating for peritube skin protection.

It is a further object of the invention to provide a coating for endotracheal tube insertion site protection.

It is a further object of the invention to provide a protective coating for tracheostomy tube insertion site protection.

It is a further object of the invention to provide a protective coating for infusion system insertion site protection.

It is a further object of the invention to provide a protective coating for condom catheter insertion site protection.

In another aspect of the invention, a coating is provided that is adherent under flex stress, including bending, twisting, and stretching.

It is a further object of the invention to provide a coating which, when applied, is water-vapor permeable.

It is a further object of the invention to provide a coating which, when applied, is oxygen permeable.

It is a further object of the invention to provide a coating that contains essential oils.

These and other objectives and advantages of the non-self-adherent compositions described herein, some of which are specifically described and others that are not, will become apparent from the detailed description and claims that follow.

DETAILED DESCRIPTION

The liquid, polymer-containing coating material described herein includes an amphiphilic polymer that includes an addition polymerizable, hydrophilic, hydroxyalkyl ester-containing monomers copolymerized with addition polymerizable hydrophobic or amphiphilic siloxysilane monomers, solubilized in a volatile solvent. The liquid, polymer-containing coating material can be used to produce an amphiphilic polymer coating on a surface by evaporating the solvent. The cast polymer coating is water insoluble and water vapor permeable, and the surface of the polymer coating is not adherent to itself or to another surface. The compositions and methods described herein have not been previously reported.

In some embodiments, the liquid, polymer-containing coating material can include about 0.1 to 50 wt % of an amphiphilic polymer dissolved in about 50 to 99.9 wt % of a volatile solvent as part of a solvent system. The amphiphilic polymer can include at least one polymerizable hydrophilic hydroxyalkyl ester-containing addition polymerizable monomer component whose homopolymer is swellable or soluble in water and at least one addition polymerizable siloxysilane-containing monomer component that is hydrophobic or amphiphilic and whose homopolymer is insoluble in water.

In some embodiments, the liquid coating material forms an adherent, conformable, water-vapor permeable, water-insoluble coating when applied to a surface. In some embodiments, the amphiphilic polymer includes about 10 to 90 weight % polymerizable hydroxyalkyl ester-containing monomer component and about 10 to 90 weight % polymerizable siloxysilane-containing monomer component.

The volatile liquid solvent can be selected from the group consisting of non-polar solvents, polar solvents and combinations thereof. In some embodiments, the non-polar solvents can be, but are not limited to, volatile linear and cyclic siloxanes, volatile alkanes, volatile cycloalkanes, volatile chlorocarbons, volatile fluorocarbons, and mixtures thereof. In some embodiments, the polar volatile solvents can be, but are not limited to, volatile alcohols, volatile esters, volatile ketones, volatile ethers, solubilized water, and mixtures thereof. In some embodiments, the volatile liquid volatilizes at room or body temperature. In some embodiments, water is not included in the volatile liquid solvent where the water is not miscible as part of the volatile solvent. As used herein, "volatile liquid" and "volatile solvent" are used interchangeably.

As used herein, non-polar solvent has its standard meaning in the art and includes solvents with molecules that contain bonds between atoms that have similar electronegativities, such as between carbon and hydrogen in hydrocarbons; bonds between atoms with similar electronegativities lack partial charges and the solvent does not have a permanent electric dipole moment, having no tendency for intramolecular association with polar species.

As used herein, polar solvent has its standard meaning in the art and includes solvents with molecules that have a large dipole moment wherein bonds between atoms of the solvent have different electronegativities, such as between oxygen and hydrogen, where there is either a permanent separation of positive and negative charges, or the centers of positive and negative charges do not coincide. Polar solvents have high dielectric constants, such as alcohols and ketones.

In some embodiments, the amphiphilic siloxysiloxane/hydroxyalkyl ester polymer and volatile solvent are present in an amount such that the liquid coating material does not adhere to a second glass surface when: (i) a first sample of the liquid coating material is applied to a first glass surface and the solvent evaporated, (ii) a second sample of the liquid coating material is applied to a second glass surface and the solvent evaporated, with the polymer coating material disposed there between, and (iii) the glass surfaces are placed together under a 500 gram weight for 24 hours at 37° C. The liquid coating material can form an adherent, conformable polymer coating when applied to a surface. The volatile liquid can volatilize at room or body temperature.

A similar behavior of non-adherence to that of glass slides under similar experimental conditions was found with gauze placed between two release liners with the amphiphilic coating cast thereon, with the gauze in contact with the two amphiphilic polymer coatings. The gauze was Fisherbrand™ Gauze Sponges by Fisher Scientific, made of 100% nonsterile cotton, and the release liner studied was by Loparex, LLC, a polyester film coated with fluorosilicone release coating. The liner was 2 mils thick.

When applied to a biological surface, such as skin, the siloxysilane/hydroxyalkyl ester polymer coating has the surprising property of not being adherent to itself when folded, or when placed against another object, such as clothing or bed sheets and blankets. No commercial liquid bandage coating has this desired feature, which is highly beneficial in the reduction of friction when stress or pressure is applied to a polymer coated wound or potential wound environment.

Polymerizable siloxysilane-containing monomer components useful in the present invention comprise free radically polymerizable hydrophobic and amphiphilic siloxysilane monomers that are water vapor and oxygen permeable. Polymerizable siloxysiloxanes that may be reacted with the hydrophilic, hydroxyalkyl ester-containing monomer to form copolymers, terpolymers, or multipolymers include, but are not limited to:

3-methacryloyloxypropyltris(trimethylsiloxy)silane (TRIS-M),
3-methacryloxypropyltris(trimethylsiloxy)silane (TRIS-M),
3-[tris(trimethylsiloxy)silyl]propyl methacrylate (TRIS-M),
3-acryloyloxypropyltris(trimethylsiloxy)silane (TRIS-A),
3-acryloyloxypropyltris(trimethylsiloxy)silane (TRIS-A),
3-[tris(trimethylsiloxy)silyl]propyl acrylate (TRIS-A),
3-methacryloyloxypropylpentamethyldisiloxane,
3-methacryloyloxypropylbis(trimethylsiloxy)methylsilane,
3-methacryloyloxypropyltris(vinyldimethylsiloxy)silane,
3-methacryloyloxy-2-hydroxypropyltris(trimethylsiloxy)silane,
(3-methacryloxy-2-hydroxypropoxy)propylbis(trimethylsiloxy)methylsilane,
3-(methacryloxy-2-(2-hydroxyethoxy)propyloxy)propylbis(trimethylsiloxy)methylsilane,
(3-methacryloxy-2-hydroxypropyloxy)propyltris(trimethylsiloxy)silane,
3-methacryloyloxymethylbis(trimethylsiloxy)(pentamethyldisiloxanyl)silane,
3-methacryloyloxyethyltris(pentamethyldisiloxanyl)silane,
3-methacryloyloxypropylpentamethyldisiloxane,
3-methacryloyloxypropyl-1,1,1-trimethyl-3,3,-diphenyldisiloxane,
3-methacryloyloxypropyl-1,1,1,3,3-pentaphenyldisiloxane,
methacryloyloxymethylbis(trimethylsiloxy)methylsilane,
methacryloyloxymethyltris(trimethylsiloxy)silane,
3-methacryloyloxypropylheptacyclopentyl-T8-silsesquioxane,
3-methacryloyloxypropylheptaisobutyl-T8-silsesquioxane,
3-acryloyloxypropylmethylbis(trimethylsiloxy)silane,
3-methacryloyloxypropyl-1,1,1-triphenyl-3,3-dimethyldisiloxane,
(methacryloxymethyl)dimethylphenylsilane,
methylbis(trimethylsiloxy)silylpropylglyceryl methacrylate,
tris(trimethylsiloxy)silylpropylglyceryl methacrylate,
3-methacrylamidopropyltris(trimethylsiloxy)silane,
3-acrylamidopropyltris(trimethylsiloxy)silane,
p-vinylphenyltris(trimethylsiloxy)silane,
p-vinyibenzyltris(trimethylsiloxy)silane,
vinyloxyethyltris(trimethylsiloxy)silane,
vinylnonyldimethyl(trimethylsiloxy)silane,
vinylnonyltris(trimethylsiloxy)silane,
vinylmethylbis(trimethylsiloxy)silane,
vinylpentamethyldisiloxane,
O-(vinyloxyethyl)-N-(tris[trimethylsiloxy]silylpropyl)urethane,
vinylphenylbis(trimethylsiloxy)silane,
vinyltris(dimethylsiloxy)silane,
vinyltris(trimethylsiloxy)silane,
and the like.

Many siloxysilane monomers are commercially available from Gelest, Inc., Morrisville, Pa.; Silar Laboratories, Wilmington, N.C.; and Fluorochem Ltd., Hadfield, Derbyshire, United Kingdom.

Polymerizable hydroxyalkyl ester-containing monomer components useful in the present invention comprise free radically polymerizable hydrophilic hydroxyl monomers whose homopolymers are swellable or soluble in water. Examples of polymerizable hydroxyalkyl ester-containing monomers that may be reacted with the hydrophobic or amphiphilic siloxysiloxane monomers to form copolymers, terpolymers, or multipolymers include, but are not limited to: hydroxyalkyl esters of acrylic acid, hydroxyalkyl esters of methacrylic acid, including hydroxyalkyl esters of 2-chloroacrylic acid, 2-bromoacrylic acid, 2-fluoroacrylic acid, 2-(trichloromethyl)acrylic acid, 2-(trifluoromethyl)acrylic acid, 2-(bromomethyl)acrylic acid and hydroxyalkyl esters of ethoxyethyl methacrylate, such as 2-(2-hydroxyethoxy)ethyl methacrylate, 2-[2-(2-hydroxyethoxy)ethoxy]ethyl methacrylate, and 2-(2-(2-(2-hydroxyethoxy)ethoxy)ethoxy)ethyl methacrylate, and combinations thereof.

In some embodiments, the polymerizable hydroxyalkyl ester containing monomer components can be 2-hydroxyethyl acrylate, 2-hydroxyethyl methacrylate (HEMA), 2- and 3-hydroxypropyl acrylate and methacrylate, 2,3-dihydroxypropyl acrylate and methacrylate, 4-hydroxybutyl acrylate and methacrylate, 2-(2-hydroxyethoxy)ethyl methacrylate, 2,3-dihydroxypropyl methacrylate (also known as 1-glycerol methacrylate, glyceryl methacrylate, and glyceryl monomethacrylate), and combinations thereof. Additionally, dihydroxyalkyl esters of unsaturated dicarboxylic acids, such as maleic acid, fumaric acid, and itaconic acid, can also be copolymerized with the siloxysilane monomer. Examples of such esters include, but are not limited to, bis(2-hydroxyethyl)maleate, bis(2-hydroxypropyl)maleate, bis(2-hydroxyethyl itaconate), bis(2-hydroxypropyl)itaconate, and bis(2,3-dihydroxypropyl)itaconate. Hydroxyalkyl esters of ethylenically unsaturated carboxylic acids, including ethacrylic acid, crotonic acid, isocrotonic acid, cinnamic acid, and similar acids of up to about 6 carbon atoms, can be utilized.

In some embodiments, the hydroxyalkyl ester monomers for copolymerization with the siloxysilane monomer are 2-hydroxyethyl methacrylate (HEMA), 2-hydroxyethyl acrylate, 2-hydroxypropyl methacrylate, 3-hydroxypropyl methacrylate, and 2-(2-hydroxyethoxy)ethyl methacrylate. In some embodiments, the hydroxyalkyl ester monomer for copolymerization is 2-hydroxyethyl methacrylate.

The HEMA monomer has been used extensively for the formation of hydrogels, with particular emphasis on the formation of soft, hydrophilic contact lens hydrogels. Excellent reviews on the use of HEMA in hydrogels are presented by J. Kopeček, *Journal of Polymer Science*: Part A: Polymer Chemistry, 2009, Vol. 47, 5929-5946 and O. Wichterle and D. Lim, *Nature*, 1960, Vol. 185, 117-118). HEMA has been a primary component of conventional hydrogels for contact lenses, such as Bausch & Lomb's Soflens 38 Contact Lens, a 38% water-containing lens crosslinked by ethylene glycol dimethacrylate. As used herein, a traditional hydrogel (without silicone- or fluorine-containing groups) is defined by a water-adsorbing polymer that adsorbs at least 38 weight % water or saline and which does not dissolve in water or saline.

For advanced silicone hydrogel contact lenses, with substantially higher oxygen permeabilities than those of conventional soft (hydrophilic) lenses (because of the presence of silicone monomers and macromonomers), HEMA may be added to the formulation, but it is not sufficiently hydrophilic to overcome the hydrophobicity and low surface free energy of silicone monomers and macromonomers that will dominate the lens surface, and other more hydrophilic monomers, such as N-vinylpyrrolidone, N,N-dimethylacrylamide, N,N-dimethylaminoethyl methacrylate, and methacrylic acid, are added to increase the surface wettability of the lenses (hydrophilicity). Such advanced silicone hydrogel contact lenses generally have a water content of at least 24 weight % to 38 weight % (Ciba Vision Air Optix Night & Day Aqua; Bausch & Lomb PureVision Contact Lens; Johnson & Johnson Acuvue® Oasys® Brand with Hydraclear® Plus). However, silicone hydrogel contact lenses are not soluble in the volatile solvents described herein.

In some embodiments, the amphiphilic polymers can have a water of hydration of less than 10 weight %.

The volatile liquid solvent for solubilizing the siloxysilane/hydroxyalkyl ester polymer and for its rapid volatilization is selected from the group consisting of non-polar solvents comprising volatile linear and cyclic siloxanes, volatile alkanes, volatile cycloalkanes, volatile chlorocarbons and volatile fluorocarbons, and polar volatile solvents comprising volatile alcohols, volatile esters, volatile ketones, volatile ethers, solubilized water, and combinations thereof.

As used herein, "hydrophobic" has its standard meaning and includes materials that repel water, are insoluble or relatively insoluble in water, and lack an affinity for water.

As used herein, "hydrophilic" has its standard meaning and includes compounds that have an affinity to water and are ionically charged or have polar groups in their structure that attract water. For example, hydrophilic compounds can be miscible, swollen, or soluble in water, or otherwise attract or have an affinity for water.

As used herein, an "amphiphilic" material has both hydrophobic and hydrophilic properties. In this invention, the amphiphilic polymer films are insoluble in deionized water.

As used herein, "volatile" has its standard meaning, that is, it can evaporate rapidly at normal temperatures and pressure. For example, a solvent can be volatile if one metric drop (1/20 mL, 50 µL) of the solvent will evaporate completely between 20-25° C. within 5 minutes, or within 4 minutes, or within 3 minutes, or within 2 minutes, or within 1 minute, or within 30 sec, or within 15 sec.

As used herein, "non-stinging" means that the composition does not cause a sharp, irritating or smarting pain as a result of contact with a biological surface.

Examples of non-polar solvents that can be used in the volatile solvent include, but are not limited to, volatile linear and cyclic siloxanes, volatile alkanes, volatile cycloalkanes, volatile chlorocarbons, volatile chlorofluorocarbons, volatile fluorocarbons, and combinations thereof.

Examples of polar solvents that can be used in the volatile solvent include, but are not limited to volatile alcohols, volatile esters, volatile ketones, solubilized water, and volatile ethers.

Specific examples of volatile nonpolar solvents include, but are not limited to linear siloxanes, such as hexamethyldisiloxane or octamethyltrisiloxane; cyclic siloxanes, such as hexamethylcyclotrisiloxane or octamethylcyclotetrasiloxane; alkanes, such as propane, butane, and isobutane (all under pressure), pentane, isopentane, 2-methylpentane, 3-methylpentane, hexane, heptane, octane, isooctane, petroleum distillates, and isomers thereof; cycloalkanes, such as cyclohexane; chlorocarbons, such as chloroform and methylene chloride; chlorofluorocarbons, such as trichloromonofluoromethane, dichlorodifluoromethane, and dichlorotetrafluoroethane; fluorocarbons, such as tetrafluoroethane, heptafluoropropane, 1,1-difluoroethane, pentafluoropropane, perfluoroheptane, perfluoromethylcyclohexane; and hydrofluoroalkanes, such as 1,1,1,2,-tetrafluoroethane and 1,1,1,2, 3,3,3-heptafluoropropane; and combinations thereof.

Specific examples of polar, volatile solvents include, but are not limited to, alcohols, such as methanol, ethanol, isopropanol, n-propanol and n-butanol; esters, such as ethyl acetate, isopropyl acetate, n-propyl acetate and n-butyl acetate; ketones, such as acetone and methyl ethyl ketone; ethers, such as tetrahydrofuran and dioxane; solubilized water; and combinations thereof.

Nonpolar solvents can be used with the polymer coatings of this invention when non-sting topical applications are preferred. Non-stinging topical applications may be preferred in application of the polymer coatings to open wounds or to damaged, burned or sensitized skin.

If antimicrobial behavior in wound care or skin treatment is desired, polar solvents, such as, ethanol and isopropanol, which can include solubilized water, can be used for their innate biocidal activity. In addition, ethanol and isopropanol can be particularly useful due to their ability to solubilize polar antimicrobial agents, which can be in their salt form. Examples of polar antimicrobial agents that are soluble in ethanol and isopropanol include, but are not limited to, chlorhexidine digluconate, chlorhexidine diacetate, poly(hexamethylene biguanide) hydrochloride, alexidine hydrochloride, silver salts, gentamicin sulfate, iodine, povidone-iodine, neomycin sulfate, polymyxin B, bacitracin, tetracyclines, clindamycin, gentamicin, nitrofurazone, mafenide acetate, silver sulfadiazine, terbinafine hydrochloride, miconazole nitrate, as well as ketoconazole, clotrimazole, itraconazole, metronidazole, and the like.

For the initiation of polymerization of the vinyl monomers, free radical initiators can be used in forming the amphiphilic polymers. Free radical initiators that may be useful include, but are not limited to, azobisisobutyronitrile, 2,2'-azobis(2,4-dimethylpentanenitrile), 2,2'-azobis-(2-methylbutanenitrile), 2,2'-azodi(2-methylbutyronitrile), 2,2'-azobis(2-methylpropionitrile), 2,2'-azodi(2,4-dimethylvaleronitrile), 2,2'-azobisamidinopropane dihydrochloride, 2,2'-azobis(2-nnethylpropionamidine)dihydrochloride, 2,2'-azobis(N,N'-dimethylene isobutyramidine)dihydrochloride, 2,2'-azobis(4-methoxy-2,4-dimethylvaleronitrile), 4,4'-azobis(4-cyanovaleric acid), potassium persulfate, ammonium persulfate, benzoyl peroxide, 2,5-dimethyl-2,5-bis(2-ethylhexanoylperoxy)hexane, acetyl peroxide, cumyl peroxide, t-butyl peroxide, t-butyl hydroperoxide, redox initiators and the like. The polymerization can be carried out by solution, emulsion, suspension or precipitation techniques. In addition to thermal initiation, polymerization can also be initiated by oxidation-reduction (redox) initiators, UV or visible light photoinitiators, ionizing radiation, plasma, sonic irradiation, electrochemical, or controlled (living radical) polymerization initiators.

If soluble block, graft, or star siloxysilane/hydroxyalkyl ester polymers are desired, these can be prepared using known techniques, which include, but are not limited to, Atom Transfer Radical Polymerization (ATRP), Reversible Addition-Fragmentation Chain Transfer Polymerization (RAFT), Stable Free Radical Polymerization (SFRP), and Nitroxide-Mediated Radical Polymerization.

Essential oils can also be added to the formulation as fragrance or aromatic agents, skin conditioning agents, and/or as antimicrobial agents. Examples of essential oils that may be useful in the liquid, polymer-containing coating materials, include, but are not limited to, thymol, menthol, sandalwood, camphor, cardamom, cinnamon, jasmine, lavender, geranium, juniper, menthol, pine, lemon, rose, *eucalyptus*, clove, orange, mint, linalool, spearmint, peppermint, lemongrass, bergamot, citronella, cypress, nutmeg, spruce, tea tree, wintergreen (methyl salicylate), vanilla, and the like. In some embodiments, the liquid, polymer-containing coating materials can include thymol, sandalwood oil, wintergreen oil and eucalyptol for antimicrobial properties and peppermint oil or pine oil for fragrance.

Emollients/moisturizers can be added to the liquid, polymer-containing coating materials to provide a soothing application to the skin or wound. Emollients/moisturizers function by forming an oily layer on the top of the skin that traps water in the skin. In some embodiments, emollients/moisturizers useful in the liquid, polymer-containing coating material include, but are not limited to, petrolatum, lanolin, mineral oil, dimethicone, dimethiconol, fluid siloxy compounds isopropyl palmitate, isopropyl myristate, isopropyl isostearate, isostearyl isostearate, diisopropyl sebacate, caprylyl glycol, propylene dipelargonate, 2-ethylhexyl isononoate, 2-ethylhexylglycerin, 2-ethylhexyl stearate, cetyl lactate, lauryl lactate, isopropyl lanolate, 2-ethylhexyl salicylate, cetyl myristate, oleyl myristate, oleyl stearate, oleyl oleate, hexyl laurate, and isohexyl laurate, lanolin, jojoba oil, olive oil, coconut oil, sunflower oil, cocoa butter, shea butter, kokum butter, octyldodecanol, hexyldecanol, dicaprylyl ether, decyl oleate, and combinations thereof.

Humectants can be added to the amphiphilic polymer coating formulations to increase water adsorption into the polymer coating. Examples of humectants useful in the liquid, polymer-containing coating material include, but are not limited to, glycerin, lecithin, 1,2-propylene glycol, dipropylene glycol, polyethylene glycol, 1,3-butylene glycol, sorbitol, urea, 1,2,6-hexanetriol, and combinations thereof.

When polar solvents are utilized as the volatile solvent, a chelating agent can be added to the polymer coating formulation to enhance antimicrobial activity by removing metal ions from the surfaces of bacteria, presumably making the microorganism more susceptible to the antimicrobial agent. In some embodiments, a chelating agent and an antimicrobial agent are included in the liquid, polymer-containing coating material. Suitable chelating agents include, but are not limited to, aminocarboxylic acids, ethylenediaminetetraacetic acid (EDTA), nitrilotriacetic acid, nitrilotripropionic acid, diethylenetriaminepentaacetic acid, 2-hydroxyethylethylenediaminetriacetic acid, cyclohexane-1,2-diaminetetraacetic acid, N-hydroxyethylethylenediaminetriacetic acid, 1,6-diaminohexamethylenetetraacetic acid, 1,2-diaminocyclohexanetetraacetic acid, ethylene glycol-O,O'-bis(2-aminoethyl)-N,N,N',N'-tetraacetic acid, 1,3-diaminopropanetetraacetic acid, N,N'-bis(2-hydroxybenzyl) ethylenediamine-N,N'-diacetic acid, ethylenediamine-N,N'-diacetic acid, ethylenediamine-N,N'-dipropionic acid, triethylenetetraaminehexaacetic acid, ethylenediamine-N, N'-bis(methylenephosphonic acid), iminodiacetic acid, N,N-bis(2-hydroxyethyl)glycine, 1,3-diamino-2-hydroxypropanetetraacetic acid, 1,2-diaminopropanetetraacetic acid, ethylenediaminetetrakis(methylenephosphonic acid), N-(2-hydroxyethyl)iminodiacetic acid and biphosphonates such as editronate, salts thereof, and combinations thereof.

Suitable chelating agents also include, but are not limited to, hydroxyalkylphosphonates as disclosed in U.S. Pat. No. 5,858,937. For example, the '937 patent discloses the tetrasodium salt of 1-hydroxyethylidene-1,1-diphosphonic acid, also referred to as tetrasodium etidronate, which is commercially available from Monsanto Company as DeQuest 2016 diphosphonic acid sodium salt or phosphonate.

Other addition polymerizable monomers may also be included in the amphiphilic polymers to modify cohesive strength, elasticity, flexibility, toughness, transparency, opaqueness, color, fluorescence, ultraviolet absorbance, increased or decreased refractive index, oxygen permeability, oxygen solubility and combinations thereof. However, other additional polymerizable monomers are only added to an extent that their inclusion into the siloxysilane/hydroxyalkyl ester polymer retains the feature of non-adherence of the surface of the polymer film to itself or to another surface. Examples of other addition polymerizable monomers that are useful in the amphiphilic polymer include, but are not limited to, derivatives of acrylic acid (acrylates), methacrylic acid (methacrylates), itaconic acid (itaconates), maleic acid (maleates), and fumaric acid (fumarates).

In some embodiments, the concentration of the added polymerizable monomer ranges from 0.1-20 weight %, while the concentration ranges from 0.5-15 weight %, or 1-10 weight % in other embodiments. The percentages of added polymerizable monomer are based on the total weight of the amphiphilic polymer. Examples of these other monomers include, but are not limited to, methyl methacrylate, methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, 1-pyrenylmethyl methacrylate, 2-naphthyl acrylate, 2-naphthyl methacrylate, 9-anthracenylmethyl methacrylate, isodecyl acrylate, isodecyl methacrylate, isooctyl acrylate, isooctyl methacrylate, isobornyl acrylate, isobornyl methacrylate, benzyl acrylate, benzyl methacrylate, 2-butoxyethyl acrylate, n-butyl acrylate, n-butyl methacrylate, ethyl acrylate, ethyl methacrylate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, t-butyl acrylate, t-butyl methacrylate, isoamyl acrylate, isoamyl methacrylate, n-pentyl acrylate, n-pentyl methacrylate, neopentyl acrylate, neopentyl methacrylate, 2-methylbutyl acrylate, 2-methylbutyl methacrylate, 1-methylbutyl acrylate and methacrylate, 1-methylpentyl acrylate and methacrylate, 2-methylpentyl acrylate and methacrylate, 3-methylpentyl acrylate and methacrylate, 2-ethylbutyl acrylate and methacrylate, 2-ethylhexyl acrylate and methacrylate, 3,5,5-trimethylhexyl acrylate and methacrylate, 3-heptyl acrylate and methacrylate, n-decyl acrylate and methacrylate, n-dodecyl acrylate and methacrylate, n-octadecyl acrylate, n-octadecyl methacrylate, 2-phenylethyl acrylate, 2-phenylethyl methacrylate, n-tridecyl methacrylate, dimethyl itaconate, diethyl itaconate, di-n-propyl itaconate, di-isopropyl itaconate, di-n-butyl itaconate, di-2-ethylhexyl itaconate, dimethyl maleate, diethyl maleate, dimethyl fumurate, diethyl fumurate, trimethylsilylmethyl methacrylate, esters of 2-ethylacrylic acid, and the like, and combinations thereof. In addition, fluorinated siloxanes, fluorinated itaconates, fluorinated acrylates or fluorinated methacrylates, such as hexafluoroisopropyl methacrylate, can also be used.

In some embodiments, hydrophilic monomers other than hydroxyalkyl (meth)acrylates, itaconates, maleates, and fumarates are included in the amphiphilic polymer. These hydrophilic monomers can be included in the amphiphilic polymer provided that they do not cause adherence of two films together, or adherence of a polymer film to another substrate. Examples of such hydrophilic monomers include, but are not limited to, acrylamide, N-(1,1-dimethyl-3-oxobutyl)acrylamide, and N-[tris(hydroxymethyl)]methacrylamide, wherein the polymers are cast from alcohol solutions.

In general, antimicrobial agents and anti-infective agents such as chlorhexidine diacetate, chlorhexidine digluconate, chlorhexidine, poly(hexamethylene biguanide) hydrochloride, alexidine dihydrochloride, benzalkonium chloride, benzethonium chloride, cetyltrimethylammonium chloride, cetylpyridynium chloride, alkyltrimethylammonium bromides, neomycin, bacitracin, polymyxin B, miconazole, clotrimazole, ketoconazole, itraconazole, metronidazole, peroxides, salicylic acid, salicylates, silver salts, zinc salts, N-halo compounds and the like can be added to the liquid, polymer-containing coating formulations based upon the use of polar, volatile solvents, such as ethanol, isopropanol, solubilized water, or combinations thereof.

The liquid, polymer-containing coating materials can be applied over a temperature range of −10° C. to +45° C. when applied to skin, wounds, nails, mucous membranes, medical devices and other inanimate objects to form films that dry rapidly. In particular, it is a property of the liquid, polymer-containing coating materials that once the coating material is applied at room temperature, the adherent coating can form in less than 5 minutes, less than 3 minutes, less than 2 minutes, less than 1 minute, less than 30 seconds or less than 15 seconds.

In some embodiments, after evaporation of the volatile solvent, the polymer coating can contain encapsulated active antimicrobial, biological, or pharmaceutical ingredients for controlled release to an underlying biological surface. In some embodiments, the active agent can be present in the cast amphiphilic polymer and can form a clear polymer film.

The polymer coating composition can also be imbibed by swabs, cloth, sponges, foams, wound dressing materials and non-woven and paper products, such as paper towels and wipes, or attached to the surface of a device, such as a catheter, by dip coating, brushing or spray coating, followed by solvent evaporation. When applied to a device or dressing, surface friction of the device or dressing is reduced. In addition, antimicrobial agents may be added to the polymer formulations to provide a coating that can be inserted into a body or placed upon a body or device in order to prevent the occurrence of microbial infection.

In some embodiments, a novel amphiphilic polymer that comprising an addition polymerizable siloxysilane monomer component and an addition polymerizable hydroxyalkyl ester monomer component is disclosed. The amphiphilic polymer can be any of the amphiphilic monomers described herein, so long as the amphiphilic polymer is soluble is at least one solvent selected from the group consisting of hexamethyldisiloxane, isooctane, isopropanol and ethanol. In contrast, the closest known polymers are insoluble in these solvents.

EXAMPLES

The following examples serve to illustrate the invention without limiting it thereby. It will be understood that variations and modifications can be made without departing from the spirit and scope of the invention.

The following abbreviations are used in this invention:

ALEX: Alexidine Dihydrochloride, (1,1-hexamethylenebis[5-(2-ethylhexyl)biguanide]dihydrochloride), Toronto Research Chemicals, Lot 4-WG-119-2.

CHA: Chlorhexidine Diacetate, (1,1'-Hexamethylenebis[5-(4-chlorophenyl)biguanide]diacetate), Spectrum Chemicals, C2295, Lot WK0817.

EDTA: Ethylenediaminetetraacetic Acid Disodium Salt, JT Baker 4040-01, Lot H25593.

ETON: Ethanol, absolute, 200 proof, ≥99.5%, Sigma-Aldrich, 459844, Lot SHBC 9545V.

EA: Ethyl Acetate, Alfa Aesar, 31344, Lot J15Y044.

HEMA: 2-Hydroxyethyl Methacrylate, 97%, Sigma Aldrich 128635, Lot MKBG2011V (with 0.155 wt % ethylene glycol dimethacrylate and 0.488% polyethylene glycol methacrylate).

HEMA°: 2-Hydroxyethyl Methacrylate, Ophthalmic Grade, >99.5%, Monomer-Polymer, 9453, Lot 23-77-22, with 0.053% ethylene glycol dimethacrylate and 0.008% polyethylene glycol methacrylate.

Hexanes: Fisher Scientific, H292-20, Lot 133813, ≥98.5%, contains various methylpentanes, 4.2%.

HMDS: Hexamethyldisiloxane, Gelest, SIH6115.0, Lot 2A-17635.

IPA: Isopropanol, <0.2% water, BDH1133-4LP, Lot 082511A.

ISO: Isooctane, BDH1155-19L, Lot 022009A.

MMT-PDMS: Monomethacryloxypropyl-terminated polydimethylsiloxane, Gelest, MCR-M17, Lot 8K-13758, 70-80 cSt.

NIPAM: N-isopropyl acrylamide, Jarchem Jii, 2210-25-5, Lot N60206.

PHMB: Poly(Hexamethylene Biguanide) Hydrochloride, Cosmocil™ CQ, Arch Chemical, Lot 137261.

SC 10: Sensiva® SC 10, Caprylyl glycol and Ethylhexylglycerin, Schülke & Mayr, Lot 1179743.

SC 50: Sensiva® SC 50, Ethylhexylglycerin, Schülke & Mayr, Lot 1191540.

TRIS-A: 3-[Tris(trimethylsiloxy)silyl]propyl Acrylate, Gelest, SIA0210.0-225GM, Lot 3J-3804.

TRIS-M: 3-[Tris(trimethylsiloxy)silyl]propyl Methacrylate, Silar, 1713, Lot 10011DC (0.36% TRIS dimer).

TRIS-M*: 3-[Tris(trimethylsiloxy)silyl]propyl Methacrylate, Silar, 1713, Lot 122109 (0% TRIS dimer).

VAZO 67: 2,2'-Azobis(2-methylbutyronitrile), Dupont, Lot 80224368.

Preparation of TRIS-M:HEMA and TRIS-A:HEMA Copolymers

All TRIS-M:HEMA and TRIS-A:HEMA copolymers were made by free radical polymerization in either ethyl acetate or isopropanol at 5, 10, or 20% monomer solids using 2,2'-azobis(2-methylbutanenitrile), holding the reaction solution at 70° C. (±2° C.) for 6 h. The monomers used were 3-[tris(trimethylsiloxy)silyl]propyl methacrylate (TRIS-M) or 3-[tris(trimethylsiloxy)silyl]propyl acrylate (TRIS-A) and 2-hydroxyethyl methacrylate (HEMA). Two forms of each monomer were used, wherein 3-[tris(trimethylsiloxy)silyl]propyl methacrylate is designated as TRIS-M when 0.36%

TRIS dimer (1,3-bis(3-methacryloxypropyl)-1,1,3,3-tetrakis (trimethylsiloxy)disiloxane) and designated as TRIS-M* when an ophthalmic grade with no TRIS dimer is present (0%), whereas 2-hydroxyethyl methacrylate is designated as HEMA when conventional HEMA with 0.155 weight % ethylene glycol dimethacrylate is present and as HEMA° when ophthalmic grade is used with a very low crosslinking content (0.053% of ethylene glycol dimethacrylate). The TRIS-A monomer was used as received. Polymerizations conducted in ethyl acetate are exemplified by Examples 1, 5, 6, 12-16, while polymerizations conducted in isopropanol are exemplified by Examples 2-4, 7-11 in Table 1. For each polymerization, the polymer in the reaction solvent was precipitated into ten-fold excess of water, filtered, washed repeatedly with water, and then dried with heat.

Preparation of TRIS-M:HEMA:NIPAM Terpolymers

Two TRIS-M:HEMA:NIPAM terpolymers were made by free radical polymerization in ethyl acetate at 20% monomer solids with 2,2'-azobis(2-methylbutanenitrile) as initiator, holding the reaction solution at 70° C. (±2° C.) for 6 h, with the monomers of 3-[tris(trimethylsiloxy)silyl]propyl methacrylate (TRIS-M), 2-hydroxyethyl methacrylate (HEMA), and N-isopropylacrylamide (NIPAM). The polymers in the reaction solvents were precipitated into ten-fold excess of water or methanol, filtered, washed repeatedly with water, and then dried with heat yielding TRIS-M:HEMA:NIPAM ratios of 50.00:37.5:12.5 and 75:12.5:12.5.

Solubilities of TRIS-M:HEMA Copolymer

The solubility of the amphiphilic 76.19:23.81 TRIS-M:HEMA copolymer (Table 1, Example 10) was studied in more detail in both non-polar and polar solvents. The non-polar solvents included hexamethyldisiloxane, isooctane, hexane, n-heptane, isododecane, hexadecane, chloroform, octamethylcyclotetrasiloxane, and decamethylcyclopentasiloxane, and the polar solvents included isopropanol, ethanol, methanol, ethyl acetate, acetone, dioxane and tetrahydrofuran. The polymer was dissolved at 5 weight % in each solvent, and each solution was clear with no precipitate or insoluble matter, yielding a clear, transparent polymer film when the solvent was cast and dried. Additionally, the 76.19:23.81 TRIS-M:HEMA copolymer was found to be soluble from 0.1 weight % to 50 weight % in the non-polar solvent of hexamethyldisiloxane and in the polar solvent of isopropanol. This polymer was insoluble in deionized water, but could be dissolved in isopropanol/water solutions containing up to 20.5 weight % water, based on the total weight of the volatile solvent.

Adhesion Studies

Polymer self-adhesion studies were conducted as follows. Polymer solutions (50 µL, 10% w/w of dried solid polymer dissolved in either HMDS or isopropanol) were pipetted onto two Loparex 10431 release liners (of polyester film coated with fluorosilicone release coating; liner is 2 mils thick). The films were allowed to dry at least 24 h at room temperature on the release liner to ensure complete removal of solvent. After drying, self-adhesion studies were conducted by placing the amphiphilic polymer coated sides of two release liners in contact or by placing a 1 inch square of two-ply cotton gauze dressing (Fisherbrand non-sterile cotton gauze) on top of a dried polymer-coated release liner. In both instances, the liners or gauze-liner were placed together under a 500 gram weight for 24 h at 37° C. After 24 h, polymer self-adhesion or polymer adhesion to gauze was evaluated on a scale of 0 to 3 (0-no adhesion, 1-mild adhesion, 2-moderate adhesion, 3-complete adhesion) by peeling the release liners away from each other or by peeling the gauze off the polymer-coated release liner.

Similar to the experimental conditions used for the adherence/non-adherence of two release liner-coated films placed together with the polymer surfaces in contact, related studies were done with two polymer coated glass slides, where the same adherence scale of 0-3 was used for no adhesion (0) to complete adhesion (3).

Polymer Solubility and Adherence/Non-Adherence

Table 1 lists the amphiphilic siloxysilane/hydroxyalkyl comonomers of TRIS-M:HEMA, TRIS-M*:HEMA°, and TRIS-A:HEMA that were copolymerized, the solubilities of the resulting polymers in non-polar, non-stinging solvents of hexamethyldisiloxane (HMDS) and isooctane (ISO), as well as in the polar, stinging solvents of isopropanol (IPA), ethanol (ETON), and ethyl acetate (EA). All polymer solutions when cast yielded clear polymer films. Following casting, all polymer films were insoluble in water. The siloxysilane monomers studied include 3-[tris(trimethylsiloxy)silyl]propyl methacrylate (TRIS-M and TRIS-M*) and its related acrylate (TRIS-A), and the hydroxyalkyl monomer studied was the monofunctional alcohol 2-hydroxyethyl methacrylate (HEMA and HEMA°). The monomers of TRIS-M and HEMA are reported to contain inherent crosslinking agents. Presumably, TRIS-A would also be crosslinked with its dimer in the same fashion as is TRIS-M since both monomers could be prepared by a similar synthesis procedure. Preferably, the total crosslinking concentration of the siloxysilane:hydroxyalkyl ester copolymer is less than 0.4 weight % of the monomers used in order to have solubility of the polymer in non-polar and polar solvents.

TABLE 1

Solubility and Film Properties of TRIS-M/HEMA and TRIS-A/HEMA

| | Ratios w/w | | | Soluble | Soluble | Soluble | Soluble | Soluble | Adhesion | Adhesion |
|---|---|---|---|---|---|---|---|---|---|---|
| Example | TRIS-M | TRIS-A | HEMA | HMDS | ISO | IPA | ETOH | EA | to Self | to Gauze |
| 1 | 10.00* | — | 90.00° | no | no | yes | yes | no | 0 | 0 |
| 2 | 20.00* | — | 80.00° | no | no | yes | yes | no | 0 | 0 |
| 3 | 25.00* | — | 75.00° | no | no | yes | yes | no | 0 | 0 |
| 4 | 33.33* | — | 66.67° | no | no | yes | yes | no | 0 | 0 |
| 5 | 50.00* | — | 50.00° | no | no | yes | yes | partial | 0 | 0 |
| 6 | 66.67 | — | 33.33 | no | no | yes | yes | yes | 0 | 0 |
| 7 | 71.43 | — | 28.57 | no | no | yes | yes | yes | 0 | 0 |
| 8 | 75.00 | — | 25.00 | no | no | yes | yes | yes | 0 | 0 |
| 9 | 75.61 | — | 24.39 | yes | yes | yes | yes | yes | 0 | 0 |
| 10 | 76.19 | — | 23.81 | yes | yes | yes | yes | yes | 0 | 0 |

TABLE 1-continued

Solubility and Film Properties of TRIS-M/HEMA and TRIS-A/HEMA

| | Ratios w/w | | | Soluble | Soluble | Soluble | Soluble | Soluble | Adhesion | Adhesion |
|---|---|---|---|---|---|---|---|---|---|---|
| Example | TRIS-M | TRIS-A | HEMA | HMDS | ISO | IPA | ETOH | EA | to Self | to Gauze |
| 11 | 77.78 | — | 22.22 | yes | yes | yes | yes | yes | 0 | 0 |
| 12 | 80.00 | — | 20.00 | yes | yes | yes | yes | yes | 0 | 0 |
| 13 | 83.33 | — | 16.67 | yes | yes | yes | yes | yes | 1 | 1 |
| 14 | 87.50 | — | 12.50 | yes | yes | yes | yes | yes | 2 | 2 |
| 15 | 90.00 | — | 10.00 | yes | yes | yes | yes | yes | 2 | 3 |
| 16 | — | 75.00 | 25.00 | no | no | yes | yes | yes | 0 | 0 |

*indicates TRIS-M with 0% dimer, °indicates ophthalmic grade HEMA with low crosslinker content From Table 1 it is seen that the 2-hydroxyethyl methacrylate (HEMA° and HEMA) copolymers, containing 2-hydroxyethyl methacrylate concentrations ranging from 90 weight % to 25 weight %, with 3-[tris(trimethylsiloxy)silyl] propyl methacrylate (TRIS-M and TRIS-M*), containing from 10.00 to 75.00 weight % siloxysilane monomer, are insoluble in the non-stinging volatile solvents of HMDS and isooctane, but are soluble in the polar alcohol and ester solvents (Examples 1-8). After solvent evaporation, the resulting polymers are clear, homogeneous, and film forming with no self-adhesion or adhesion to gauze. These characteristics are beneficial for liquid-based polymer coatings that are applied to intact skin, potentially damaged skin, pre- and post-surgical sites, and inanimate medical devices, or where enhanced antimicrobial behavior is needed in conjunction with moisture vapor transmission and, where needed, with oxygen transmission. In addition, the use of isopropanol and ethanol as solvents could enhance the solubility of polar antimicrobial agents in the liquid-based polymer coating solution.

Relative to the solubility behavior of the amphiphilic copolymers of TRIS and N-isopropylacrylamide (NIPAM) (U.S. Pat. No. 7,795,326, Examples 1, 2, and 5), polymer concentrations of TRIS:NIPAM related to Examples 5, 7 and 8 of Table 1 were found to be soluble in the non-stinging, non-polar solvent of hexamethyldisiloxane, where those of TRIS-M:HEMA were not.

For TRIS-M concentrations greater than 75 wt % to 90 wt %, with corresponding HEMA concentrations less than 25 wt % to 10 wt % (Examples 9-15), these polymers are soluble in both the nonpolar solvents of HMDS and isooctane, as well as the polar solvents of isopropanol and of ethanol. This family of siloxysilane/hydroxyalkyl ester polymers has the greatest solubility in both polar and non-polar solvents.

The TRIS-M:HEMA copolymer films of Examples 1-12 display no self-adhesion or adhesion to gauze, whereas those polymer films with greater than 80 wt % siloxane monomer and less than 20 wt % hydroxyalkyl ester monomer (Examples 13-15) have mild to moderate adherent properties. Furthermore, from Table 1 it is seen that the acrylate copolymer of TRIS-A with HEMA (Example 16) displays similar properties to its methacrylate analog (Example 8).

Interestingly, a comparison was made for the surface tack of the TRIS-M:HEMA and TRIS-A:HEMA copolymers to the occurrence of self-adhesion and gauze adhesion (Table 2). Tack was determined by pressing an index finger on a dried polymer film on a glass slide for 3 seconds and rating on a scale from 0 to 5 (0=no tack, 1=light tack, 2=mild tack, 3=moderate tack, 4=tacky, 5=very tacky). This process has also been used for measuring surface tack of various siloxane-based liquid bandages (U.S. Pat. No. 8,491,881; U.S. Pat. No. 8,263,720; U.S. Pat. No. 8,197,803; U.S. Pat. No. 7,641,893).

TABLE 2

Tack, Self-Adhesion, and Gauze Adhesion of TRIS-M:HEMA and TRIS-A:HEMA

| | Composition % Monomer Ratios w/w | | | | Adhesion to | Adhesion to |
|---|---|---|---|---|---|---|
| Example | TRIS-M | TRIS-A | HEMA | Tack | Self | Gauze |
| 17 | 10.00* | — | 90.00° | 0 | 0 | 0 |
| 18 | 20.00* | — | 80.00° | 0 | 0 | 0 |
| 19 | 25.00* | — | 75.00° | 0 | 0 | 0 |
| 20 | 33.33* | — | 66.67° | 0 | 0 | 0 |
| 21 | 50.00* | — | 50.00° | 0 | 0 | 0 |
| 22 | 66.67 | — | 33.33 | 0.50 | 0 | 0 |
| 23 | 71.43 | — | 28.57 | 0.50 | 0 | 0 |
| 24 | 75.00 | — | 25.00 | 0.50 | 0 | 0 |
| 25 | 75.61 | — | 24.39 | 0.33 | 0 | 0 |
| 26 | 76.19 | — | 23.81 | 0.50 | 0 | 0 |
| 27 | 77.78 | — | 22.22 | 0 | 0 | 0 |
| 28 | 80.00 | — | 20.00 | 0.67 | 0 | 0 |
| 29 | 83.33 | — | 16.67 | 2 | 1 | 1 |
| 30 | 87.50 | — | 12.50 | 3 | 2 | 2 |
| 31 | 90.00 | — | 10.00 | 4 | 2 | 3 |
| 32 | — | 75.00 | 25.00 | 0.17 | 0 | 0 |

From Table 2 it is noted that several of the TRIS-M:HEMA (Examples 22-26, 28) and TRIS-A:HEMA (Example 32) copolymer films have a detectable but low level of tack (0.67 and below) while maintaining no self-adhesion nor any adhesion to gauze at 37° C. This demonstrates a lack of correlation between surface tack and the ability of the siloxane:hydroxyalkyl ester monomers to have either self-adhesive or gauze adhesive properties. This data is particularly relevant in demonstrating that such polymer coatings on skin or a wound would not cause adherence to clothing, bed sheets, blankets, wound dressing materials, etc., even where a low degree of surface tack is present, thereby decreasing trauma resulting from frictional and pressure forces upon the polymer coatings.

Properties of 50.00:37.5:12.5 TRIS:HEMA:NIPAM Terpolymer

In U.S. Pat. No. 7,795,326, J. C. Salamone et al. reported liquid, polymer-containing coating materials that comprise an amphiphilic polymer of a polymerizable, nitrogen-containing, hydrophilic monomer, which may give thermoresponsive properties, and which is copolymerized with a hydrophobic, polymerizable siloxy-containing monomer, in a solvent system of a volatile hydrophobic, non-polar liquid that is non-stinging to a user and wherein the material forms a coating or bandage in the form of a film when applied to a surface or the skin of a user. The volatile, hydrophobic, non-polar solvents are non-stinging, volatile, hydrophobic liquids selected from the group consisting of volatile linear and cyclic siloxanes, volatile alkanes, volatile fluorocarbons, liquid and supercritical carbon dioxide, and mixtures thereof. The preferable hydrophobic polymerizable siloxy-containing monomer component is 3-methacryloyloxypropyltris(trimethylsiloxy)silane (TRIS-M, also named 3-[tris(trimethylsiloxy)silyl]propyl methacrylate) and the preferable hydrophilic polymerizable nitrogen-containing monomer component is N-isopropylacrylamide (NIPAM). The reported tack of a 3:1 TRIS:NIPAM copolymer (75:25 TRIS-M:NIPAM) (Examples 33-37, esp. Exp. 31) was 2 on a scale of 5, with 5 being the most tacky.

The tack, self-adhesion, and gauze adhesion of 50.00:37.5:12.5 weight % TRIS-M:HEMA:NIPAM terpolymer were determined to ascertain the effect of having both hydrophilic monomers copolymerized with hydrophobic TRIS-M. The tack of this terpolymer was zero, its self-adherence also had a value of zero, and there was no gauze adhesion. Related to the data in Table 2, the HEMA monomer apparently lowers the surface tack of a NIPAM monomer when copolymerized with TRIS-M.

Preparation and Solubility of TRIS-M:HEMA:MMT-PDMS Macromolecular Monomer

Macromolecular siloxane monomers, such as monovinyl-terminated polydimethylsiloxane, mono(methacryloxypropyl)-terminated polydimethylsiloxane, or mono(methacryloxy-2-hydroxypropyl)-terminated polydimethylsiloxane and the like, which are used extensively in the preparation of high oxygen permeability silicone hydrogel contact lenses, are not preferred for copolymerization with hydroxyalkyl ester monomers because they lower the modulus of the polymer coating, increasing its surface attachment to other materials and to itself, in addition to not being film forming. However, such monofunctional macromonomers can be terpolymerized in low concentration with a lower molecular weight siloxysilane monomer, such as TRIS-M and with a hydroxyalkyl ester monomer, such as 2-hydroxyethyl methacrylate (HEMA). Divinyl-terminated polydimethylsiloxanes, such as α,ω-dimethacryloyloxypropylpolydimethylsiloxane and related multifunctional macromolecular monomers, which are also used extensively in silicone hydrogel contact lenses, both for oxygen permeability and covalent crosslinking, are contraindicated for polymerization with a siloxylsilane monomer and a hydroxyalkyl ester monomer because of extensive crosslinking of the amphiphilic polymers of this invention, resulting in polymer insolubility in all solvents and, hence, having no ability to function as liquid-based polymer coating formulations.

A terpolymer of TRIS:HEMA:MMT-PDMS 71.43:23.81:4.76 was synthesized at 20% solids in ethyl acetate in a procedure related to the above for TRIS:HEMA. The resulting copolymer had a finger tack of 0, a gauze adhesion of 0, and self-adhesion of 0.5 on release liner. The terpolymer was soluble in IPA, ETOH, and ethyl acetate, and was film forming when cast. It was insoluble in HMDS and ISO. Thus, with a low concentration of the monofunctional PDMS macromonomer, its behavior appears similar to that of Examples 7 and 8 of Table 1, although with some self-adherence.

Water-Uptake

Oxygen permeable contact lens technology includes numerous inventions related to siloxane monomers and siloxane macromonomers with various wetting agents, including HEMA. Both soft and rigid (hard) oxygen permeable, optically clear contact lenses are crosslinked to maintain their designed shape for optical requirements, using both low molecular weight and macromolecular crosslinking agents. Such copolymer systems may swell in solvents, but do not dissolve. The addition of wetting agents to oxygen permeable contact lenses is critically needed to prevent attachment of the contact lens to the cornea, in addition to facilitating lubricity for movement of the eye lid over the contact lens. Furthermore, contact lens surface hydrophilicity is needed to prevent dry spots on the lens that hinder vision in addition to hindering protein denaturation on the lens surface and to prevent lipid adsorption, causing lens dryness, overall discomfort, and potential sites for bacterial accumulation. Because of the high hydrophobicity of siloxane monomers and macromonomers for high oxygen permeability contact lenses, surface wetting agent monomers and polymers of greater hydrophilicity than HEMA are often utilized (U.S. Pat. No. 6,367,929, Background of the Invention).

Table 3 presents the % water uptake of 75:25 TRIS-M:HEMA, 80:20 TRIS:HEMA, and 75:12.5:12.5 TRIS:HEMA:NIPAM after soaking in deionized water for 4 days at 37° C. TRIS-M*:HEMA° of higher HEMA° content turned opaque under these conditions, and were thus not examined further (Table 1, Examples 1-4). In Example 1 of U.S. Pat. No. 7,795,326 the uptake of saline of 3:1 TRIS-M:NIPAM copolymer air-dried films of the polymers absorbed 394% of their weight of saline at 20° C. and 127% of their weight of saline at 30° C., the latter temperature being above the Lower Critical Solution Temperature of the NIPAM component (causing polymer contraction).

Table 3 shows that the water uptake of 75:25 TRIS-M:HEMA and 80:20 TRIS:HEMA was less than 5 wt %, while the water uptake of the TRIS:HEMA:NIPAM terpolymers was higher at 15.7 wt %, again indicating the higher hydrophilicity of NIPAM to HEMA. Importantly, this is further confirmed by a comparison of the high saline uptake of the 3:1 TRIS-M copolymer of Example 1 of U.S. Pat. No. 7,795,326 relative to the low water uptake of the TRIS-M:HEMA copolymers, with the TRIS-M:NIPAM polymer having saline adsorption of from 28 times to 87 times that of the TRIS:HEMA copolymers. While many ionic polymers display lower saline uptake compared to deionized water uptake, for neutral polymers such as that in Table 3, the uptake differences between saline and deionized water are expected to be slight.

TABLE 3

Water Uptake of TRIS-M:HEMA and TRIS-M:HEMA:NIPAM

| Example | Composition % Monomer Ratios w/w | | | Water Uptake % w/w |
|---|---|---|---|---|
| | TRIS-M | HEMA | NIPAM | |
| 33 | 75.00 | 25.00 | — | 4.6 |
| 34 | 80.00 | 20.00 | — | 2.7 |
| 35 | 75.00 | 12.50 | 12.50 | 15.7 |

Surface Lubricity/Wettability

A study of the surface lubricity and surface wettability of several TRIS-M:HEMA copolymers was conducted. The copolymer compositions studied included Examples 1-15 of Table 1. The polymer films, were cast onto glass slides from isopropyl alcohol (IPA) for Examples 1-8 and from HMDS for Examples 9-15. The polymer films were then soaked at 37° C. in water for 24 h. Examples 5-15 remained clear, while 1-4 turned opaque. All film surfaces felt rough and none had a slippery, lubricious feeling. Additionally and surprisingly, all the TRIS-M:HEMA copolymer film surfaces were non-wetting when treated with water. The higher HEMA content films became translucent after soaking in water. Films with lower HEMA content had a rougher surface than films with higher HEMA content. Thus, none of the polymer films studied displayed hydrogel characteristics, including those of high HEMA° content (Examples 1-4), which is in contrast to the original HEMA soft contact lens that contains 38% water or silicone hydrogel contact lens materials.

Alcohol-Based Antimicrobial Coatings

Traditional siloxane-based liquid bandage polymer coatings have been developed from inert, volatile solvents, which are principally hexamethyldisiloxane (HMDS) and isooctane (ISO, also named 2,2,4-trimethylpentane), because of their non-stinging behavior and high volatility to deposit a coating quickly when applied to damaged skin and wounds. Most antimicrobial agents are polar and are often in salt form, precluding solubility in either non-polar HMDS or ISO. Certain neutral, non-polar antimicrobial agents can, however, dissolve in such non-polar solvents (see isopropylxanthic disulfide, A. B. Salamone, et al., U.S. Pat. No. 5,103,812, Example 25). Apparently, isopropylxanthic disulfide liberates a toxic gas in contact with water (Sigma Aldrich, product number 452688), and antimicrobial agents with a greater safety profile are desired.

In order to greatly increase the antimicrobial efficacy of a siloxane liquid-based polymer coating, an alcohol-based solvent (e.g., ethanol, isopropanol, and n-propanol) is preferable, because of its inherent antimicrobial behavior. Such a siloxane polymer coating allows moisture vapor transmission and, when needed, oxygen permeability. The alcohol solvent could rapidly diminish any microorganisms attached to the device. Such compositions are highly effective in pre- and post-surgical applications, as well as depositing the polymer coatings on inert devices. Previous siloxane liquid bandage solutions could incorporate up to 10% alcohol, but the antimicrobial behavior of an alcohol solution normally requires at least 50-60% alcohol/water to be antimicrobial (K. H. Diehl, et al., U.S. Pat. No. 5,591,442).

Additionally, the use of alcohol or alcohol/water solvents could greatly augment the solubility of many topical biologically-active agents in the siloxane-hydroxyalkyl ester liquid applied polymer coatings. For example, such biologically-active agents include, but are not limited to, antimicrobial agents, antibacterial agents, anti-infective agents, antifungal agents, antiprotozoal agents, anti-inflammatory agents, antiviral agents, antitumor agents, antibiotics, birth control agents, antipruritic agents, anti-smoking agents, motion-sickness agents, antibiotics, anesthetic agents, psoriasis agents, dermatitis agents, acne agents, astringent agents, chronic pain agents, non-steroidal anti-inflammatory (NSAIDs) agents, liposomes, lipid nanoparticles, blood pressure agents, heart regulating agents, steroids, saccharides, polysaccharides, nucleotides, peptides, growth factors, cytokines, essential oils, skin care additives, emollients, humectants, vitamins, antioxidants, combinations thereof, and the like.

In general, antimicrobial agents (or anti-infective agents) such as chlorhexidine and its salts, poly(hexamethylene biguanide) and its salts, alexidine and its salts, benzalkonium chloride, benzethonium chloride, cetyltrimethylammonium chloride, cetylpyridinium chloride, alkyltrimethylammonium bromides, neomycin, bacitracin, polymyxin B, miconazole, clotrimazole, ketoconazole, itraconazole, metronidiazole, peroxides, salicylic acid, salicylates, silver salts, zinc salts, N-halo compounds and the like, separately and in combination, are utilized in biocidal topical formulations and have solubility in alcohol and alcohol/water solvents.

Representative examples of antibiotics that may be included in the coating materials described herein include, but are not limited to, penicillins, cephalosporins such as cefadroxil, cefazolin, cefaclor, aminoglycosides such as gentamycin and tobramycin, sulfonamides such as sulfamethoxazole, and metronidazole. Representative examples of anti-inflammatory agents include: steroids such as prednisone, prednisolone, hydrocortisone, adrenocorticotropic hormone, and sulfasalazine; and non-steroidal anti-inflammatory drugs (NSAIDs) such as aspirin, ibuprofen, naproxen, fenoprofen, indomethacin, and phenylbutazone.

Representative examples of antiviral agents that may be included in the coating materials described herein include, but are not limited to, acyclovir, ganciclovir, zidovudine. Representative examples of antifungal agents include: nystatin, ketoconazole, griseofulvin, flucytosine, miconazole, clotrimazole, itraconazole and metronidiazole.

Representative examples of antiprotozoal agents that may be included in the coating materials described herein, include, but are not limited to, pentamidine isethionate, quinine, chloroquine, and mefloquine. Representative examples of anti-infective agents include, but are not limited to, silver oxide and silver salts, chlorhexidine, alexidine, and poly(hexamethylene biguanide).

Pain medications that can be incorporated into the alcohol-based siloxysiloxane:hydroxyalkyl ester polymer coatings include, but are not limited to, nortriptyline and amitriptyline; anticonvulsants such as gabapentin, pregabalin, and carbamazepine; serotonin-norepinephrine reuptake inhibitors such as duloxetine and venlafaxine; opiates such as oxycodone and tramadol; cannabinoids such as nitinol; and topical medications such as lidocaine, pramocaine, benzocaine, and capsaicin.

Table 4 shows the effect of the incorporation of chlorhexidine diacetate (CHA) into isopropanol solutions in the absence of water on several TRIS-M:HEMA (Examples 36-39) and TRIS-A:HEMA (Example 40) copolymer solutions and cast films. All cast polymer films were optically clear. In solution, over 2 wt % of CHA was solubilized in the copolymer isopropanol solutions and, when cast and dried, the clear, transparent films encapsulated between 18-19 weight % CHA.

TABLE 4

CHA Incorporation into TRIS-M/HEMA and TRIS-A/HEMA

| Example | Composition % Monomer Ratios w/w | | | % CHA Solution | % CHA Film | Solution |
| --- | --- | --- | --- | --- | --- | --- |
| | TRIS-M | TRIS-A | HEMA | | | |
| 36 | 66.67 | — | 33.33 | 2.12 | 19.29 | clear |
| 37 | 75.00 | — | 25.00 | 2.02 | 18.34 | clear |
| 38 | 76.19 | — | 23.81 | 2.00 | 18.19 | clear |
| 39 | 80.00 | — | 20.00 | 2.10 | 19.11 | clear |
| 40 | — | 75.00 | 25.00 | 2.12 | 19.26 | clear |

Related to the incorporation of CHA into TRIS-M:HEMA polymer solutions and dried films, the polymeric biguanide PHMB was incorporated into TRIS-M:HEMA using an isopropanol/water solvent (Table 5). By a comparison of Example 38 of Table 4 with Examples 41 and 42 of Table 5, it is seen that substantially less of the polymeric antimicrobial biguanide PHMB was incorporated into the solutions and the films than that of the dimeric biguanide analog CHA.

TABLE 5

PHMB Incorporated into TRIS-M/HEMA 76.19/23.81

| | Composition % Monomer Ratios w/w | | | Solution Composition % w/w | | | | % Active | |
|---|---|---|---|---|---|---|---|---|---|
| Example | TRIS-M | HEMA | Active | Polymer | IPA | Water | PHMB | Film | Solution |
| 41 | 76.19 | 23.81 | PHMB | 9.961 | 89.653 | 0.383 | 0.002 | 0.02 | clear |
| 42 | 76.19 | 23.81 | PHMB | 8.155 | 73.393 | 18.359 | 0.092 | 1.12 | clear |

To demonstrate the sustained release of an antimicrobial agent from the siloxysilane/hydroxyalkyl ester polymer films, a zone of inhibition (ZOI) study was performed with CHA in TRIS-M:HEMA for the following microorganisms: *Pseudomonas aeruginosa* (ATCC 27853), *Staphylococcus epidermidis* (ATCC 12228), *Escherichia coli* (ATCC 8739), and *Candida albicans* (ATCC 10231) (Table 6). ZOI testing was conducted by INCELL Corporation, LLC of San Antonio, Tex. Testing was conducted for a period of seven days. The positive control was 2% chlorhexidine diacetate dissolved in 90/10 IPA/ETOH or 70/30 IPA/Water, the test material was a solution of 9% TRIS-M:HEMA 75/25 with 2% chlorhexidine diacetate dissolved in 91/9 IPA/ETOH (yielding 18.34% encapsulated CHA), and the negative control was 90/10 IPA/ETOH solvent or untreated.

For the Gram-negative bacteria *Pseudomonas aeruginosa*, the Gram-positive bacteria of *Staphylococcus epidermidis*, the Gram-negative bacteria of *Escherichia coli* and the yeast of *Candida albicans*, the zones of inhibition of their negative controls in each case for each day were zero. For films of TRIS-M:HEMA:CHA with *Staphylococcus epidermidis* and *Candida albicans*, both polymer film zones of inhibition over 7 days were similar to their positive controls, while for *Escherichia coli* the TRIS-M:HEMA:CHA polymer film was somewhat more effective as a biocidal agent than its positive control. Thus, for each microorganism, a controlled delivery of CHA antimicrobial from the TRIS-M:HEMA polymer was demonstrated to be as effective as a solution of CHA that was non-encapsulated by polymer, wherein both the initial polymer solution and the CHA non-polymer solutions had a similar CHA content.

TABLE 6

Zone of inhibition in $cm^2$

| | P. aeruginosa Day | | | | | | | S. epidermidis Day | | | | | | |
|---|---|---|---|---|---|---|---|---|---|---|---|---|---|---|
| Test Material | 1 | 2 | 3 | 4 | 5 | 6 | 7 | 1 | 2 | 3 | 4 | 5 | 6 | 7 |
| Positive Control- 2% CHA in 90/10 IPA/ETOH | — | — | — | — | — | — | — | 1.4 | 2.1 | 3.5 | 4.8 | 7.8 | 5.9 | 5.4 |
| Positive Control- 2% CHG in 70/30 IPA/Water | 3.7 | 3.8 | 4.2 | 4.8 | 5.0 | 4.6 | 4.7 | — | — | — | — | — | — | — |
| Polymer with 2% CHA in IPA/ETOH | 4.2 | 4.7 | 4.5 | 5.1 | 5.3 | 5.3 | 5.5 | 1.2 | 1.7 | 1.9 | 5.9 | 6.2 | 5.2 | 6.0 |
| Negative Control- 90/10 IPA/ETOH | — | — | — | — | — | — | — | 0.0 | 0.0 | 0.0 | 0.0 | 0.0 | 0.0 | 0.0 |
| Negative Control- Untreated | 0.0 | 0.0 | 0.0 | 0.0 | 0.0 | 0.0 | 0.0 | — | — | — | — | — | — | — |

| | E. coli Day | | | | | | | C. albicans Day | | | | | | |
|---|---|---|---|---|---|---|---|---|---|---|---|---|---|---|
| Test Material | 1 | 2 | 3 | 4 | 5 | 6 | 7 | 1 | 2 | 3 | 4 | 5 | 6 | 7 |
| Positive Control- 2% CHA in 90/10 IPA/ETOH | 1.5 | 1.8 | 1.3 | 1.5 | 1.8 | 1.8 | 1.7 | 3.1 | 2.9 | 2.9 | 2.9 | 3.1 | 3.3 | 3.0 |
| Positive Control- 2% CHG in 70/30 IPA/Water | — | — | — | — | — | — | — | — | — | — | — | — | — | — |
| Polymer with 2% CHA in IPA/ETOH | 1.9 | 2.0 | 2.0 | 2.1 | 2.0 | 1.9 | 2.0 | 3.1 | 2.9 | 2.8 | 3.0 | 2.9 | 3.0 | 3.0 |
| Negative Control- 90/10 IPA/ETOH | 0.0 | 0.0 | 0.0 | 0.0 | 0.0 | 0.0 | 0.0 | 0.0 | 0.0 | 0.0 | 0.0 | 0.0 | 0.0 | 0.0 |
| Negative Control- Untreated | — | — | — | — | — | — | — | — | — | — | — | — | — | — |

To demonstrate further the ability of alcohol-based solutions of siloxane:hydroxyalkyl ester polymers to provide encapsulation of biologically-active agents when cast from isopropanol or ethanol solvents, Table 7 demonstrates that biologically-active agents can be encapsulated into siloxane: hydroxyalkyl ester polymers in alcohol solvents, and that the resulting solutions are clear with no insoluble matter and the polymer coatings are clear and film forming. The biologically-active agents include various antimicrobial agents, essential oils, skin care additives, emollients, humectants, a local anesthetic and a vitamin/antioxidant.

TABLE 7

Actives Incorporated into TRIS-M/HEMA 76.19/23.81

| | Composition % Monomer Ratios w/w | | | % Active | % Active | Solvent | |
|---|---|---|---|---|---|---|---|
| Example | TRIS-M | HEMA | Active | Solution | Film | % w/w | Solution |
| 43 | 76.19 | 23.81 | Alexidine | 0.064 | 0.60 | 100 ETOH | clear |
| 44 | 76.19 | 23.81 | Benzethonium chloride | 0.025 | 0.23 | 100 IPA | clear |
| 45 | 76.19 | 23.81 | Cineole | 0.18 | 1.70 | 100 IPA | clear |
| 46 | 76.19 | 23.81 | Clotrimazole | 1.05 | 2.52 | 100 IPA | clear |
| 47 | 76.19 | 23.81 | Lauricidin | 0.20 | 1.66 | 100 ETOH | clear |
| 48 | 76.19 | 23.81 | Lidocaine | 1.02 | 5.30 | 100 IPA | clear |
| 49 | 76.19 | 23.81 | Sensiva SC10 | 0.55 | 5.22 | 100 IPA | clear |
| 50 | 76.19 | 23.81 | Sensiva SC50 | 0.71 | 6.64 | 100 IPA | clear |
| 51 | 76.19 | 23.81 | Tea tree oil | 6.35 | 40.41 | 100 IPA | clear |
| 52 | 76.19 | 23.81 | Vitamin E | 1.11 | 10.09 | 100 IPA | clear |

Additionally, the chelating agent EDTA was incorporated into TRIS-M:HEMA polymer solutions and dried films using an isopropanol/water solvent (Table 8). The resulting EDTA concentration in the dried film is 0.10%.

TABLE 8

EDTA Incorporated into TRIS-WHEMA 76.19/23.81

| | Composition % Monomer Ratios w/w | | | Solution Composition % w/w | | | | % Active | |
|---|---|---|---|---|---|---|---|---|---|
| Example | TRIS-M | HEMA | Active | Polymer | IPA | Water | EDTA | Film | Solution |
| 53 | 76.19 | 23.81 | EDTA | 9.958 | 89.624 | 0.397 | 0.021 | 0.10 | clear |

In Table 9 are presented various medical devices that have been coated with 8.99 weight % of a 76.16:23.81 TRIS/HEMA copolymer (Table 1, Example 10) containing 2 weight % chlorhexidine diacetate in 91/9 weight % IPA/ETOH solvent. These medical devices include wound dressings, with and without chlorhexidine digluconate (CHG), a dressing for antimicrobial protection to the skin surrounding a catheter insertion site (catheter-related blood stream infections), catheters, a guiding sheath, a V.A.C. (Vacuum Assisted Closure®) accessory for negative pressure wound therapy, and bioactive glass for bone repair.

The coatings were prepared as follows: For ConvaTec Aquacel®, CVS Calcium Alginate Dressing, CVS Rolled Gauze, and Covidien Kendall™ AMD Antimicrobial Foam Dressing, 100 μL of polymer solution was placed on each material and let air dry overnight. For Ethicon Biopatch and Novabone® 45S5 Bioglass, 50 μL of polymer solution was placed on each material and let air dry overnight. For Terumo Pinnacle™ Introducer Sheath tubing, Navilyst Bioflo™ PICC 45-872 catheter, and Cook Spectrum Turbo-Ject® PICC catheters (G03812 and G54479), the polymer solution was swabbed onto the surface of each material and let air dry for 20 minutes. For KCl V.A.C. VeraLink™ Cassette tube, the tube was cut open, and the polymer solution was swabbed onto the inner surface of the tube and let air dry for 20 minutes. All materials were weighed before and after treatment. The particles of Novabone® Bioglass, which was in powder form, were glued together, while the dressings of Covidien Kendall™ AMD Antimicrobial Foam Dressing, CVS Calcium Alginate Dressing, CVS Sterile Premium Rolled Gauze, and Ethicon Biopatch, adsorbed the polymer coating solution into the surfaces of the dressings. The weight gain for all materials is presented in Table 9 where, depending on the material, the weight gain was from 35.08% for cotton gauze (Example 59) to 0.031% for the V.A.C. tubing (Example 61).

TABLE 9

Coated Medical Devices

| Example | Device | Weight Gain % |
|---|---|---|
| 54 | ConvaTec Aquacel ® | 29.65 |
| 55 | Cook Spectrum Turbo-Ject ® PICC G03812 Catheter | 1.00 |
| 56 | Cook Spectrum Turbo-Ject ® PICC G54479 Catheter | 0.86 |
| 57 | Covidien Kendall ™ AMD Antimicrobial Foam Dressing | 4.32 |
| 58 | CVS Calcium Alginate Dressing | 26.13 |
| 59 | CVS Sterile Premium Rolled Gauze | 35.08 |
| 60 | Ethicon Biopatch ® | 13.44 |
| 61 | KCI V.A.C. VeraLink ™ Cassette Tube | 0.31 |
| 62 | Navilyst BioFlo ™ PICC 45-872 Catheter | 1.06 |
| 63 | Novabone ® 45S5 Bioglass | 5.34 |
| 64 | Terumo Pinnacle ™ Introducer Sheath | 0.87 |

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

We claim:

1. A liquid, polymer-containing coating material, comprising an amphiphilic polymer dissolved in a volatile solvent, said amphiphilic polymer comprising about 10 to 90 weight % of at least one addition polymerizable siloxysilane-containing monomer and about 10 to 90 weight % of at least one addition polymerizable hydroxyalkyl ester-containing monomer.

2. The liquid, polymer-containing coating material according to claim 1, wherein each of said at least one addition polymerizable hydroxyalkyl ester-containing monomer forms a homopolymer that is swellable or soluble in water, and each of said at least one addition polymerizable siloxysilane-containing monomers forms a homopolymer that is hydrophobic or amphiphilic and insoluble in water.

3. The liquid, polymer-containing coating material according to claim 1, comprising about 0.1 to 50 wt-% of said amphiphilic polymer and about 50 to 99.9 wt-% on said volatile solvent, wherein said weight percentages are based on the total weight of the liquid, polymer-containing coating material.

4. The liquid, polymer-containing coating material according to claim 3, wherein each of said at least one addition polymerizable hydroxyalkyl ester-containing monomer forms a homopolymer that is swellable or soluble in water, and each of said at least one addition polymerizable siloxysilane-containing monomers forms a homopolymer that is hydrophobic or amphiphilic and insoluble in water;

wherein said liquid coating material forms an adherent, conformable, water-vapor permeable, water-insoluble coating when applied to a surface, wherein the amphiphilic polymer comprises about 10 to 90 weight % of said at least one addition polymerizable hydroxyalkyl ester-containing monomer and about 10 to 90 weight % of said at least one polymerizable siloxysilane-containing monomer component; and wherein said volatile solvent is selected from the group consisting of non-polar solvents comprising volatile linear and cyclic siloxanes, volatile alkanes, volatile cycloalkanes, volatile chlorocarbons, volatile fluorocarbons and combinations thereof, and polar volatile solvents comprising volatile alcohols, volatile esters, volatile ketones, volatile ethers, solubilized water, and combinations thereof.

5. The liquid, polymer-containing coating material according to claim 3 wherein each of said at least one addition polymerizable hydroxyalkyl ester-containing monomers forms a homopolymer that is swellable or soluble in water, and each of said at least one addition polymerizable siloxysilane-containing monomers forms a homopolymer that is hydrophobic or amphiphilic and insoluble in water;

wherein said liquid coating material forms an adherent, conformable, water-vapor permeable, water-insoluble coating when applied to a surface, wherein the amphiphilic polymer comprises about 20 to 90 weight % of said at least one addition polymerizable hydroxyalkyl ester-containing monomer and about 10 to 80 weight % of said at least one polymerizable siloxysilane-containing monomer; and wherein said volatile solvent is selected from the group consisting of volatile linear and cyclic siloxanes, volatile alkanes, volatile cycloalkanes, volatile chlorocarbons, volatile fluorocarbons, and polar volatile solvents comprising volatile alcohols, volatile esters, volatile ketones, volatile ethers, solubilized water and combinations thereof, wherein said liquid coating material does not adhere to itself when: (i) a first sample of the liquid coating material is applied to a first surface and the solvent evaporated, and (ii) a second sample of the liquid coating material is applied to a second surface and the solvent evaporated, with the polymer coating material disposed there between, and (iii) the two polymer-coated surfaces are placed together under a 500 gram weight for 24 hours at 37° C., and wherein said volatile solvent volatilizes at room or body temperature.

6. The liquid, polymer-containing coating material according to claim 3, wherein each of said at least one addition polymerizable hydroxyalkyl ester-containing monomers forms a homopolymer that is swellable or soluble in water, and each of said at least one addition polymerizable siloxysilane-containing monomers forms a homopolymer that is hydrophobic or amphiphilic and insoluble in water;

wherein said liquid coating material forms an adherent, conformable, water-vapor permeable, water-insoluble coating when applied to a surface, wherein the amphiphilic polymer comprises about 20 to 90 weight % of said at least one addition polymerizable hydroxyalkyl ester-containing monomer and about 10 to 80 weight % of said at least one additional polymerizable siloxysilane-containing monomer component; and wherein said volatile solvent is selected from the group consisting of non-polar solvents comprising volatile linear and cyclic siloxanes, volatile alkanes, volatile cycloalkanes, volatile chlorocarbons, volatile fluorocarbons, and combinations thereof, and polar volatile solvents comprising volatile alcohols, volatile esters, volatile ketones, volatile ethers, solubilized water, and combinations thereof, wherein said liquid coating material does not adhere to gauze when: (i) the liquid coating material is applied to a first surface and the solvent evaporated, and (ii) gauze is placed into contact with the polymer coating material disposed there between, and (iii) the gauze covered polymer surface is placed under a 500 gram weight for 24 hours at 37° C., and wherein said volatile solvent volatilizes at room or body temperature.

7. The liquid, polymer-containing coating material according to claim 1, wherein said hydrophobic polymerizable siloxy-containing monomer component is selected from the group consisting of addition polymerizable alkylsiloxysilanes, alkylaryisiloxysilanes, and arylsiloxysilanes.

8. The liquid, polymer-containing coating material according to claim 7, wherein said hydrophobic polymerizable siloxysilane-containing monomer component is selected from 3-[tris(trimethylsiloxy)silyl]propyl methacrylate and 3-[tris(trimethylsiloxy)silyl]propyl acrylate.

9. The liquid, polymer-containing coating material in accordance with claim 1, wherein said hydrophilic hydroxyalkyl ester-containing addition polymerizable monomer component is selected from hydroxyl alkyl esters of acrylic acid, methacrylic acid, itaconic acid, maleic acid, fumaric acid, ethacrylic acid, crotonic acid, isocrotonic acid, and cinnamic acid.

10. The liquid, polymer-containing coating material according to claim 9, wherein said hydrophilic hydroxyalkyl ester-containing addition polymerizable monomer component is selected from 2-hydroxyethyl methacrylate and 2-hydroxyethyl acrylate.

11. The liquid, polymer-containing coating material according to claim 1, wherein said hydrophilic hydroxyalkyl ester-containing addition polymerizable monomer component is 2-hydroxyethyl methacrylate and said hydrophobic addition polymerizable siloxy-containing monomer component is 3-[tris(trimethylsiloxy)silyl]propyl methacrylate.

12. The liquid, polymer-containing coating material according to claim 1, wherein the volatile solvent comprises a non-polar solvent selected from the group consisting of hexamethyldisiloxane, isooctane, chloroform, octamethylcyclotetrasiloxane, decamethylcyclopentasiloxane, and combinations thereof.

13. The liquid, polymer-containing coating material according to claim 1, wherein the volatile solvent comprises a polar solvent selected from the group consisting of isopropanol, ethanol, methanol, ethyl acetate, acetone, dioxane, tetrahydrofuran, and combinations thereof.

14. The liquid, polymer-containing coating material according to claim 13, comprising from 0.1 to 20.5 wt-% of solubilized water as part of the volatile solvent.

15. The liquid, polymer-containing coating material according to claim 1, further comprising a biologically-active agent selected from the group consisting of antimicrobial agents, antibacterial agents, anti-infective agents, antifungal agents, antiprotozoal agents, anti-inflammatory agents, antiviral agents, antitumor agents, antibiotics, birth control agents, antipruritic agents, anti-smoking agents, motion-sickness agents, antibiotics, anesthetic agents, psoriasis agents, dermatitis agents, acne agents, astringent agents, chronic pain agents, non-steroidal anti-inflammatory (NSAIDs) agents, liposomes, lipid nanoparticles, blood pressure agents, heart regulating agents, steroids, saccharides, polysaccharides, nucleotides, peptides, growth factors, cytokines, essential oils, skin care additives, emollients, humectants, vitamins, antioxidants, and combinations thereof.

16. The liquid, polymer-containing coating material according to claim 15, wherein said biologically-active agent is an antimicrobial agent.

17. The liquid, polymer-containing coating material according to claim 16, wherein said antimicrobial agent is selected from the group consisting of chlorhexidine, chlorhexidine salts, chlorhexidine diacetate, chlorhexidine digluconate, polyhexamethylene biguanide hydrochloride, polyhexamethylene biguanide salts, alexidine hydrochloride, alexidine salts, benzalkonium chloride, benzethonium chloride, cetyltrimethylammonium chloride, cetylpyridinium chloride, alkyltrimethylammonium bromides, neomycin, bacitracin, polymyxin B, miconazole, clotrimazole, ketoconazole, itraconazole, metronidazole, lidocaine, pramocaine, benzocaine, capsaicin, peroxides, salicylic acid, salicylates, silver salts, zinc salts, N-halo compounds, and combinations thereof.

18. The liquid, polymer-containing coating material according to claim 1, wherein:
said addition polymerizable siloxysilane-containing monomer comprises 3-[tris(trimethylsiloxy)silyl]propyl methacrylate,
said addition polymerizable hydroxyalkyl ester-containing monomer comprises 2-hydroxyethyl methacrylate, and
said volatile solvent is selected from the group consisting of isopropanol, ethanol, solubilized water and combinations thereof;
wherein said liquid, polymer-containing material comprises an antimicrobial agent selected from the group consisting of chlorhexidine diacetate, chlorhexidine digluconate, chlorhexidine salts, chlorhexidine, polyhexamethylene biguanide hydrochloride, polyhexamethylene salts, alexidine hydrochloride, alexidine salts, benzalkonium chloride, benzethonium chloride, miconazole, clotrimazole, ketoconazole, itraconazole, metronidazole, neomycin, silver salts, zinc salts, and combinations thereof.

19. The liquid, polymer-containing coating material according to claim 1,
wherein said additional polymerizable hydroxyalkyl ester-containing monomer comprises 2-hydroxyethyl methacrylate,
wherein said additional polymerizable siloxysilane-containing monomer comprises 3-[tris(trimethylsiloxy)silyl]propyl methacrylate,
wherein said amphiphilic polymer further comprises N-isopropylacrylamide, and
wherein said volatile solvent comprises a polar solvent selected from the group consisting of isopropanol, ethanol, dissolved water, and combinations thereof.

20. The liquid polymer-containing coating material according to claim 1 comprising a chelating agent selected from the group consisting of ethylenediaminetetraacetic acid (EDTA), aminocarboxylic acids, nitrilotriacetic acid, nitrilotripropionic acid, diethylenetriaminepentaacetic acid, 2-hydroxyethylethylenediaminetriacetic acid, cyclohexane-1,2-diaminetetraacetic acid, N-hydroxyethylethylenediaminetriacetic acid, 1,6-diaminohexamethylenetetraacetic acid, 1,2-diaminocyclohexanetetraacetic acid, ethylene glycol-O,O'-bis(2-aminoethyl)-N,N,N',N'-tetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, N,N-bis(2-hydroxyethyl)glycine, 1,3-diamino-2-hydroxypropanetetraacetic acid, 1,2-diaminopropanetetraacetic acid, ethylenediaminetetrakis (methylenephosphonic acid), N-(2-hydroxyethyl)iminodiacetic acid, biphosphonates, disodium editronate, salts thereof, and combinations thereof.

21. A method of applying an adherent coating to a surface, comprising:
applying a liquid, polymer-containing coating material to a surface, wherein said liquid, polymer-containing coating material comprises an amphiphilic polymer dissolved in a volatile solvent, wherein said amphiphilic polymer comprises about 10 to 90 weight % of at least one addition polymerizable siloxysilane-containing monomer and about 10 to 90 weight % of at least one addition polymerizable hydroxyalkyl ester-containing monomer, and
evaporating said volatile solvent.

22. The method according to claim 21, wherein said liquid, polymer-containing coating material comprises about 0.1 to 50 wt-% of said amphiphilic polymer and about 50 to 99.9 wt-% of said volatile solvent, wherein said weight percentages are based on the total weight of the liquid, polymer-containing coating material,
wherein each of said at least one addition polymerizable hydroxyalkyl ester-containing monomers forms a homopolymer that is swellable or soluble in water, and
each of said at least one addition polymerizable siloxysilane-containing monomers forms a homopolymer that is hydrophobic or amphiphilic and insoluble in water;
wherein said liquid coating material forms an adherent, conformable, water-vapor permeable, water-insoluble coating when applied to a surface,
wherein the amphiphilic polymer comprises about 20 to 90 weight % of said at least one addition polymerizable hydroxyalkyl ester-containing monomer and about 10 to 80 weight % of said at least one polymerizable siloxysilane-containing monomer; and wherein said volatile solvent is selected from the group consisting of volatile linear and cyclic siloxanes, volatile alkanes, volatile cycloalkanes, volatile chlorocarbons, volatile fluorocarbons, and polar volatile solvents comprising volatile alcohols, volatile esters, volatile ketones, volatile ethers, solubilized water and combinations thereof, wherein said liquid coating material does not adhere to a second surface when: (i) a first sample of the liquid coating material is applied to a first surface and the solvent evaporated, and (ii) a second sample of the liquid coating material is applied to a second surface and the solvent evaporated, with the polymer coating material disposed there between, and (iii) the two polymer-coated surfaces are placed together under a 500 gram weight for 24 hours at 37° C., and wherein said coating material forms an adherent, conformable polymer coating when applied to a surface, wherein said volatile liquid volatilizes at room or body temperature.

23. The method according to claim 21, wherein said applying step comprises application by at least one of spraying, wiping, dipping, painting, brushing, casting, and aerosol spraying.

24. The method according to claim 21, wherein said liquid, polymer-containing coating material comprises a biologically-active agent selected from the group consisting of antimicrobial agents, antibacterial agents, anti-infective agents, antifungal agents, antiprotozoal agents, anti-inflammatory agents, antiviral agents, antitumor agents, antibiotics, birth control agents, antipruritic agents, anti-smoking agents, motion-sickness agents, antibiotics, anesthetic agents, psoriasis agents, dermatitis agents, acne agents, astringent agents, chronic pain agents, non-steroidal anti-inflammatory (NSAIDs) agents, liposomes, lipid nanoparticles, blood pressure agents, heart regulating agents, steroids, saccharides, polysaccharides, nucleotides, peptides, growth factors, cytokines, essential oils, skin care additives, emollients, humectants, vitamins, antioxidants, and combinations thereof, and wherein said biologically-active agent is released to the surface.

25. The method according to claim 24, wherein said biologically-active agent is an antibiotic or antimicrobial agent, and said method comprises eliminating at least one microorganism on said surface.

26. The method according to claim 21, wherein said surface is a surface of a medical device selected from the group consisting of needles, tubing, membranes, ostomy pouches, dialysis catheters, central venous catheters, thoracic drain catheters, urinary catheters, angioplasty balloon catheters, surgical implants, coronary stents, prostheses, artificial limbs, whole blood oxygenators, hemodialysis membranes, blood oxygenation membranes, artificial pancreas membranes, diagnostic devices, biosensor devices, blood filters, temperature monitors, cannulae, implantable pumps, dialyzers, drainage products, electrodes, stethoscopes, fracture fixation devices, guide wires, ceramics, bioglass, pins, retention cuffs, screws, surgical instruments, valves, balloons, batteries, orthopedic implants, pacemakers, plugs, plates, ports, prosthetic heart valves, shunts, and vascular access devices.

27. The method according to claim 21, wherein said surface is a surface of an adjunctive medical material selected from the group consisting of sutures, dressings, sheets, bed clothes, clothing, undergarments, blankets, towels, pillows, surgical drapes, gowns, socks, curtains, cotton, nylon, polyester, wool, nonwoven materials, polyethylene, silicone, polypropylene, poly(methyl methacrylate), leather, elastomers, biodegradable materials, and combinations thereof.

28. A kit comprising a liquid, polymer-containing coating material according to claim 1.

29. An amphiphilic polymer comprising about 10 to 90 weight % of an addition polymerizable siloxysilane monomer component and about 10 to 90 weight % of an addition polymerizable hydroxyalkyl ester monomer component, wherein the amphiphilic polymer is soluble is at least one solvent selected from the group consisting of hexamethyldisiloxane, isooctane, isopropanol and ethanol.

* * * * *